US007892770B2

(12) United States Patent
Cao (Brian) et al.

(10) Patent No.: US 7,892,770 B2
(45) Date of Patent: Feb. 22, 2011

(54) MONOCLONAL ANTIBODY WHICH BINDS CMET (HGFR) IN FORMALIN-FIXED AND PARAFFIN-EMBEDDED TISSUES AND RELATED METHODS

(75) Inventors: Boliang Cao (Brian), Ada, MI (US); George F. Vande Woude, Ada, MI (US); Beatrice S. Knudsen, Seattle, WA (US)

(73) Assignees: Van Andel Research Institute, Grands Rapids, MI (US); Fred Hutchinson Cancer Research Center, Seattle, WA (US)

( * ) Notice: Subject to any disclaimer, the term of this patent is extended or adjusted under 35 U.S.C. 154(b) by 546 days.

(21) Appl. No.: 11/845,023

(22) Filed: Aug. 24, 2007

(65) Prior Publication Data

US 2009/0053737 A1 Feb. 26, 2009

(51) Int. Cl.
| C07K 16/30 | (2006.01) |
| C12N 5/20 | (2006.01) |
| C12P 21/08 | (2006.01) |
| G01N 33/543 | (2006.01) |
| G01N 33/554 | (2006.01) |
| G01N 33/563 | (2006.01) |
| G01N 33/574 | (2006.01) |
| G01N 33/577 | (2006.01) |

(52) U.S. Cl. .................. 435/7.23; 435/7.1; 435/7.95; 435/40.5; 435/40.51; 435/40.52; 435/70.21; 435/330; 435/331; 435/334; 435/344; 435/975; 436/501; 436/503; 436/518; 436/519; 436/548; 530/387.7; 530/387.9; 530/388.22; 530/388.8; 530/391.1; 530/391.3

(58) Field of Classification Search .............. 435/7.1, 435/7.23, 7.95, 40.5, 40.51, 40.52, 70.21, 435/330, 331, 334, 344, 975; 436/501, 503, 436/518, 519, 548; 530/387.7, 387.9, 388.22, 530/388.8, 391.1, 391.3
See application file for complete search history.

(56) References Cited

U.S. PATENT DOCUMENTS 5,917,017 A * 6/1999 Collier et al. ............... 530/350
6,939,670 B2 * 9/2005 Pressman et al. ............ 435/4

OTHER PUBLICATIONS

Press et al., 2002. Comparison of different antibodies for detection of progesterone receptor in breast cancer. Steroids 67: 799-813.*
Hellström et al., 1985. In Monoclonal Antibodies for Cancer Detection and Therapy (Baldwin et al, eds.), Academic Press, London. p. 20.*
Rudikoff et al., 1982. Single amino acid substitution altering antigen-binding specificity. Proc. Natl. Acad. Sci. USA 79: 1979-1983.*
Garcia S, et al. c-Met overexpression in inflammatory breast carcinomas: automated quantification on tissue microarrays. British Journal of Cancer 96 (No. 2):329:335 (Jan. 29, 2007).

Knudsen B, et al. A Novel Multipurpose Monoclonal Antibody for Evaluating Human c-Met Expression in Preclinical and Clinical Settings. Applied Immunohistochemistry and Molecular Morphology 17 (No. 1):57-67 (Jan. 1, 2009).
Anonymous. Data Sheet c-MET (Hepatocyte Growth Factor Receptor) mouse monoclonal antibody (NCL-cMET). <http://bsd.leica-microsystems.com/pdfs/prodoucts/cmet-u.pdf>. Retrieved by PCT Examiner Jan. 21, 2009.
Anonymous. Mouse anti-MET/HGFR monoclonal antibody. Millipore Chemicon Product Datasheet. <http://www.millipore.com/publications.nsf/a73664f9f981af8c852569b9005b4eee/adcea46db8846cbc852573060073f967/$FILE/MAB3729>. Retrieved by PCT Examiner Jan. 21, 2009.
Anonymous. Met (C-28): sc-161. Santa Cruz Biotechnology Product Datasheet. <http://datasheets.scbt.com/sc-161.pdf>. Retrieved by PCT Examiner Jan. 21, 2009.
Zhuang Z, et al. Trisomy 7-harbouring non-random duplication of the mutant MET allele in hereditary papillary renal carcinomas. Nature Genetics 19: 66-69 (Aug. 1998).
Zou Hy, et al. An Orally Available Small-Molecule Inhibitor of c-Met, PF-2341066, Exhibits Cytoreductive Antitumor Efficacy through Antiproliferative and Antiangiogenic Mechanisms. Cancer Res 67 (No. 9): 4408-4417 (May 1, 2007).
Alstock RT, et al. Algorithms for Quantitation of Protein Expression Variation in Normal Versus Tumor Tissue as a Prognostic Factor in Cancer: Met Oncogene Expression, and Breast Cancer as a Model. Cytometry 41: 155-165 (2000).
Baykal C, et al. Overexpression of the c-Met/HGF receptor and its prognostic significance in uterine cervix carcinomas. Gynecologic Oncology 88:123-129 (2003).
Birchmeier C, et al. Met, Metastasis, Motility and More. Nature Reviews Molecular Cell Biology 4: 915-925 (Dec. 2003).
Chen D, et al. Syndecan-1 Expression in Locally Invasive and Metastatic Prostate Cancer. Urology 63: 402-407 (2004).
Di Renzo MF, et al. Overexpression and Amplification of the Met/HGF Receptor Gene during the Progression of Colorectal Cancer. Clinical Cancer Research 1:147-154 (Feb. 1995).
Di Renzo MF, et al. Somatic mutations of the MET oncogene are selected during metastatic spread of human HNSC carcinomas. Oncogene 19: 1547-1555 (2000).
Fischer U, et al. Amplification of the MET Gene in Glioma. Genes Chromosomes & Cancer 12: 63-65 (1995).

(Continued)

*Primary Examiner*—Shafiqul Haq
*Assistant Examiner*—James L Grun
(74) *Attorney, Agent, or Firm*—Price, Heneveld, Cooper, DeWitt & Litton, LLP

(57) ABSTRACT

In a wide variety of human solid tumors, an aggressive, metastatic phenotype and poor clinical prognosis are associated with expression of the receptor tyrosine kinase Met. Disclosed herein are (a) a monoclonal antibody named Met4, which antibody is specific for Met, and (b) a hybridoma cell line that produces Met4. The Met4 antibody is particularly useful for detecting Met in formalin-fixed tissue. Methods of using the Met4 antibody for detection, diagnosis, prognosis, and evaluating therapeutic efficacy are provided.

16 Claims, 10 Drawing Sheets

OTHER PUBLICATIONS

Furge KA, et al. Met receptor tyrosine kinase: enhanced signaling through adapter proteins. Oncogene 19: 5582-5589 (2000).

Gherardi E, et al. Functional map and domain structure of MET, the product of the c-met protooncogene and receptor for hepatocyte growth factor/scatter factor. Proc Natl Acad Sci USA 100 (No. 21): 12039-12044 (Oct. 14, 2003).

Gmyrek GA, et al. Normal and Malignant Prostate Epithelial Cells Differ in Their Response to Hepatocyte Growth Factor/Scatter Factor. American Journal of Pathology 159 (No. 2): 579-590 (Aug. 2001).

Gotte M, et al. An expression signature of syndecan-1 (CD138), E-cadherin and c-met is associated with factors of angiogenesis and lymphangiogenesis in ductal breast carcinoma in situ. Breast Cancer Research 9 (No. 1): R8 (2007).

Grant DS, et al. Scatter factor induces blood vessel formation in vivo. Proc Natl Acad Sci USA 90: 1937-1941 (Mar. 1993).

Huang TJ, et al. Overexpression of the c-met Protooncogene in Human Gastric Carcinoma—Correlation to Clinical Features. Acta Oncologica 40 (No. 5): 638-643 (2001).

Humphrey PA, et al. Hepatocyte Growth Factor and Its Receptor (c-MET) in Prostatic Carcinoma. American Journal of Pathology 147 (No. 2): 386-396 (Aug. 1995).

Ide T, et al. The Hypoxic Environment in Tumor-Stromal Cells Accelerates Pancreatic Cancer Progression via the Activation of Paracrine Hepatocyte Growth Factor/c-Met Signaling. Annals of Surgical Oncology 14 (No. 9): 2600-2607 (2007).

Jeffers M, et al. The mutationally activated Met receptor mediates motility and metastasis. Proc Natl Acad Sci USA 95: 14417-14422 (Nov. 1998).

Jeffers M, et al. Activating mutations for the Met tyrosine kinase receptor in human cancer. Proc Natl Acad Sci USA 94: 11445-11450 (Oct. 1997).

Kang JY, et al. Tissue Microarray Analysis of Hepatocyte Growth Factor/Met Pathway Components Reveals a Role for Met, Matriptase, and Hepatocyte Growth Factor Activator Inhibitor 1 in the Progression of Node-negative Breast Cancer. Cancer Research 63: 1101-1105 (Mar. 1, 2003).

Kaposi-Novak P, et al. Met-regulated expression signature defines a subset of human hepatocellular carcinomas with poor prognosis and aggressive phenotype. Journal of Clinical Investigation 116 (No. 6): 1582-1595 (Jun. 2006).

Knudsen BS, et al. High Expression of the Met Receptor in Prostate Cancer Metastasis to Bone. Urology 60: 1113-1117 (2002).

Kuniyasu H, et al. Frequent amplification of the c-met gene in scirrhous type stomach cancer. Biochemical and Biophysical Research Communications 189 (No. 1): 227-232 (Nov. 30, 1992).

Lee JH, et al. A novel germ line juxtamembrane Met mutation in human gastric cancer. Oncogene 19: 4947-4953 (2000).

Lengyel E, et al. c-Met overexpression in node-positive breast cancer identifies patients with poor clinical outcome independent of Her2/neu. Int. J. Cancer 113: 678-682 (2005).

Lo Muzio L, et al. Effect of c-Met Expression on Survival in Head and Neck Squamous Cell Carcinoma. Tumour Biol 27: 115-121 (2006).

Lutterbach B, et al. Lung Cancer Cell Lines Harboring MET Gene Amplification Are Dependent on Met for Growth and Survival. Cancer Research 67 (No. 5): 2081-2088 (Mar. 1, 2007).

Ma PC, et al. Functional Expression and Mutations of c-Met and Its Therapeutic Inhibition with SU11274 and Small Interfering RNA in Non-Small Cell Lung Cancer. Cancer Research 65 (No. 4): 1479-1488 (Feb. 15, 2005).

Ma PC, et al. c-MET Mutational Analysis in Small Cell Lung Cancer: Novel Juxtamembrane Domain Mutations Regulating Cytoskeletal Functions. Cancer Research 63: 6272-6281 (Oct. 1, 2003).

Ma PC, et al. c-Met: Structure, functions and potential for therapeutic inhibition. Cancer and Metastasis Reviews 22: 309-325 (2003).

Martens T, et al. A Novel One-Armed Anti-c-Met Antibody Inhibits Glioblastoma Growth In vivo. Clin Cancer Res 12 (No. 20): 6144-6152 (Oct. 15, 2006).

Moon YW, et al. Missense Mutation of the MET Gene Detected in Human Glioma. Mod Pathol 13 (No. 9): 973-977 (2000).

Naldini L, et al. Scatter factor and hepatocyte growth factor are indistinguishable ligands for the MET receptor. The EMBO Journal 10 (No. 10): 2867-2878 (1991).

Peschard P, et al. Mutation of the c-Cbl TKB Domain Binding Site on the Met Receptor Tyrosine Kinase Converts It into a Transforming Protein. Molecular Cell 8: 995-1004 (Nov. 2001).

Pozner-Moulis S, et al. Antibody validation by quantitative analysis of protein expression using expression of Met in breast cancer as a model. Laboratory Investigation 87: 251-260 (2007).

Pozner-Moulis S, et al. Met, the Hepatocyte Growth Factor Receptor, Localizes to the Nucleus in Cells at Low Density. Cancer Res 66 (No. 16): 7976-7982 (Aug. 15, 2006).

Puri N, et al. c-Met Is a Potentially New Therapeutic Target for Treatment of Human Melanoma. Clin Cancer Res 13 (No. 7): 2246-2253 (Apr. 1, 2007).

Puri N, et al. A Selective Small Molecule Inhibitor of c-Met, PHA665752, Inhibits Tumorigenicity and Angiogenesis in Mouse Lung Cancer Xenografts. Cancer Res 67 (No. 8): 3529-3534 (Apr. 15, 2007).

Ridler T, et al. Picture Thresholding Using an Iterative Selection Method. IEEE Transactions on Systems, Man, and Cybernetics SMC 8 (No. 8): 630-632 (Aug. 1978).

Rong S, et al. Invasiveness and metastasis of NIH 3T3 cells induced by Met-hepatocyte growth factor/scatter factor autocrine stimulation. Proc Natl Acad Sci USA 91: 4731-4735 (May 1994).

Rosario M, et al. How to make tubes: signaling by the Met receptor tyrosine kinase. Trends in Cell Biology 13 (No. 6): 328-335 (Jun. 2003).

Rosen EM, et al. Scatter Factor and Its Relationship to Hepatocyte Growth Factor and met. Cell Growth & Differentiation 2: 603-607 (Nov. 1991).

Sawada K, et al. c-Met Overexpression Is a Prognostic Factor in Ovarian Cancer and an Effective Target for Inhibition of Peritoneal Dissemination and Invasion. Cancer Res 67 (No. 4): 1670-1679 (Feb. 15, 2007).

Schmidt L, et al. Germline and somatic mutations in the tyrosine kinase domain of the MET proto-oncogene in papillary renal carcinomas. Nature Genetics 16: 68-73 (May 1997).

Shi SR, et al. Antigen Retrieval Techniques: Current Perspectives. The Journal of Histochemistry & Cytochemistry 49 (No. 8): 931-937 (2001).

Shinomiya N, et al. RNA Interference Reveals that Ligand-Independent Met Activity Is Required for Tumor Cell Signaling and Survival. Cancer Research 64: 7962-7970 (Nov. 1, 2004).

Smolen GA, et al. Amplification of MET may identify a subset of cancers with extreme sensitivity to the selective tyrosine kinase inhibitor PHA-665752. Proc Natl Acad Sci USA 103 (No. 7): 2316-2321 (Feb. 14, 2006).

Tolgay Ocal I, et al. Tissue Microarray-Based Studies of Patients with Lymph Node Negative Breast Carcinoma Show that Met Expression Is Associated with Worse Outcome but Is Not Correlated with Epidermal Growth Factor Family Receptors. Cancer 97 (No. 9): 1841-1848 (May 1, 2003).

Tsarfaty I, et al. Alteration of Met Protooncogene Product Expression and Prognosis in Breast Carcinomas. Analytical and Quantitative Cytology and Histology 21 (No. 5): 397-408 (Oct. 1999).

Van Leenders G, et al. Intermediate Cells in Normal and Malignant Prostate Epithelium Express c-MET: Implications for Prostate Cancer Invasion. The Prostate 51: 98-107 (2002).

Welm AL, et al. MET and MYC cooperate in mammary tumorigenesis. Proc Natl Acad Sci USA 102 (No. 12): 4324-4329 (Mar. 22, 2005).

Zhang YW, et al. Hepatocyte growth factor/scatter factor mediates angiogenesis through positive VEGF and negative thrombospondin 1 regulation. Proc Natl Acad Sci USA 100 (No. 22): 12718-12723 (Oct. 28, 2003).

* cited by examiner

A.

B.

SEQUENCE LISTING

<160> NUMBER OF SEQ ID NOS: 12

<210> SEQ ID NO 1
<211> LENGTH: 1390
<212> TYPE: PRT
<213> ORGANISM: Homo sapiens

<400> SEQUENCE: 1

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160
```

```
Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
```

```
                    580                 585                 590
Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                    645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                    675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                    725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                    755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                    805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                    835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                    885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                    915                 920                 925

Gln Asn Phe Thr Gly Leu Ile Ala Gly Val Val Ser Ile Ser Thr Ala
                930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                    965                 970                 975

Thr Pro His Leu Asp Arg Leu Val Ser Ala Arg Ser Val Ser Pro Thr
                980                 985                 990

Thr Glu Met Val Ser Asn Glu Ser  Val Asp Tyr Arg Ala  Thr Phe Pro
                995                  1000                 1005
```

-continued

```
Glu Asp Gln Phe Pro Asn Ser Ser Gln Asn Gly Ser Cys Arg Gln
    1010                1015                1020

Val Gln Tyr Pro Leu Thr Asp Met Ser Pro Ile Leu Thr Ser Gly
    1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390
```

```
<210> SEQ ID NO 2
<211> LENGTH: 11
<212> TYPE: PRT
<213> ORGANISM: Homo sapiens
<220> FEATURE:
<221> NAME/KEY: MISC_FEATURE
<223> OTHER INFORMATION: region of extracellular domain of human Met

<400> SEQUENCE: 2

Ser Tyr Ile Asp Val Leu Pro Glu Phe Arg Asp
1               5                   10

<210> SEQ ID NO 3
<211> LENGTH: 10
<212> TYPE: PRT
<213> ORGANISM: Homo sapiens
<220> FEATURE:
<221> NAME/KEY: MISC_FEATURE
<223> OTHER INFORMATION: region of extracellular domain of human Met

<400> SEQUENCE: 3

Phe Leu Leu Asp Ser His Pro Val Ser Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 4

Thr Pro Pro Asn Ser Val Asp Ile Leu Pro Ser Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 5

Ala His Gly Pro Phe Asp His Leu Pro Glu Leu His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 6

Ser Met Trp Asp Phe Glu Pro Ser Ser Arg Pro Arg
1               5                   10

<210> SEQ ID NO 7
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 7

Met Ser Gln Asp Trp His Pro Asp Leu Arg Val Leu
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 8

Gln Pro Leu Arg His His Gln Asp Trp Ala Pro Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 9

Asp Trp Asp Pro Ser Tyr Arg His Arg Pro Pro Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 10

Ser Pro Cys Val Asp Trp Gly Pro His Arg Ala Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 11

Ala Trp Ser Asp Trp Ser Pro Ser Ser Arg Gln Thr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: random peptide from phage display library

<400> SEQUENCE: 12

Thr Ile Arg Pro Asp Trp Ser Pro Ala Leu Arg Ala
1               5                   10
```

MONOCLONAL ANTIBODY WHICH BINDS CMET (HGFR) IN FORMALIN-FIXED AND PARAFFIN-EMBEDDED TISSUES AND RELATED METHODS

FIELD OF THE INVENTION

The present invention is in the field of molecular diagnostics and medicine.

BACKGROUND OF THE INVENTION

The c-Met receptor kinase regulates cellular proliferation, migration, differentiation and branching morphogenesis during development and homeostasis[1-3]. Met is also expressed on the cell surface of a variety of human primary solid tumors and in their metastases (www.vai.org/met/). The amino acid sequence of the extracellular domain of human Met is provided in SEQ ID NO:1, amino acids 25-567. In its activated state, the Met receptor controls growth, invasion, and metastasis of cancer cells through multiple signal transduction pathways[4]. In some cancer cell lines, loss of Met expression through silencing promotes apoptosis, demonstrating that Met is necessary for survival[5-7]. Met activity increases through mutations in the kinase or juxtamembrane domains[8-11], through overexpression[12, 13], or through binding to its ligand, hepatocyte growth factor (HGF/SF)[14, 15]. Activating mutations of Met in the germline, which stimulate ligand-independent Met activation, are the cause for development of hereditary papillary renal carcinomas[10]. In cancerous cells, selective amplification of the mutated Met allele further enhances overall Met kinase activity[16]. The magnitude of Met expression predicts the aggressiveness of a number of cancer types (www.vai.org/met/). Accurate detection and quantification of Met protein expression are needed to identify cancers that are likely responsive to Met inhibitors and the development of such molecular diagnostics lags significantly behind the drug development.

High level expression of c-Met has been associated with poor prognosis in many cancer types, including breast, gastric, cervix, hepatocellular and head and neck[17-22]. Approximately 25% of ovarian cancers and 11% of gliomas express high levels of c-Met. In breast cancer, c-Met expression is observed in a subset of cancers independent of Her2, but is associated with increased cell proliferation[23,24]. In ductal breast cancer, simultaneous expression of Syndecan-1, E-cadherin and c-Met enhances angiogenesis and lymphangiogenesis[25]. Any disease associated with c-Met expression is referred to herein as a "Met-related disease". However, the reliability of the immunohistochemical studies has been questioned in light of the lot-to-lot variability of the antiserum raised against the C-terminal peptide in the c-Met receptor, that has been used in most studies[26]. Most commercially available Met antibodies are unreliable (or have not been stringently tested for their reliability). In addition to increased c-Met expression, elevated HGF/SF concentrations in the tumor microenvironment have also been associated with adverse outcome. For example hypoxic tumor stromal cells in pancreatic cancer increase HGF secretion and accelerate pancreatic cancer progression[27].

Mesenchymal cell lines with engineered c-Met and HGF expression are highly metastatic and expression of mutant c-Met receptor or amplification of the c-Met locus in cells lines increases the proliferative, invasive and metastatic phenotype of cancers[6, 28-30]. Together with Myc, wild type c-Met causes mammary carcinogenesis[31]. c-Met is one of the most frequently genetically altered or otherwise dysregulated receptor tyrosine kinases (RTK) in advanced human cancers and thus represents an attractive treatment target. Kinase activating c-Met mutations are observed in sporadic renal, lung, head and neck, hepatocellular carcinoma, non small cell lung cancer (NSCLC), gastric cancer and melanoma[13, 32-35]. Furthermore, amplification of the c-Met locus has been detected in gastric, metastatic colorectal and esophageal adenocarcinoma[12, 13], additional Met-related diseases. Activation of c-Met in cancer cells induces the secretion of angiogenic factors, such as VEGFA and IL-8 and inhibits synthesis of thrombospondin-1, an anti-angiogenic factor[36, 37]. In addition, c-Met activation in endothelial cells causes angiogenesis. While the cytotoxic effects of inhibiting Met activity may only occur in cancers with activated c-Met, the antiangiogenic effect may exist more frequently.

A major advance occurred with the development of small molecule inhibitors of c-Met that are orally bioactive ("Met-inhibiting agents"). Of these inhibitors, PF-2341066 demonstrates specificity for inhibition of c-Met and anaplastic lymphoma kinase (ALK) and leads to regression of of GTL-16 gastric cancer xenografts and NCI-H441 NSCLC xenografts at a dose of 50 mg/kg/day[38]. At this dose, c-Met is completely inhibited and maximal drug efficacy with long duration is achieved. Preclinical studies with one-armed anti-c-Met antibodies and small molecule kinase inhibitors[7, 39, 40] as well as early clinical studies in patients further highlight the promise of c-Met inhibitors against a variety of cancer types, their favorable pharmacodynamic properties and low toxicity. Thus, when used to treat cancers with an active Met axis, these drugs may indeed benefit many cancer patients. However, the molecular diagnostic tools to identify cancers that possess active Met pathways are not available.

Molecular diagnostics to detect expression and determine the activation state of treatment targets of kinase inhibitors are urgently needed to improve the treatment of cancer patients. Drugs that bind cell surface receptors or permeate into cells and inhibit receptor and non-receptor kinases show immense promise in the clinic, however the detection of the corresponding targets in human cancers provides a major challenge. Besides the Hercept test for quantitative measurement of Her-2/Neu expression, which required a lengthy and arduous development for use in routine clinical samples and FDA approvement, no validated diagnostic tests for receptor or non-receptor protein kinase expression are available. The difficulty in developing these diagnostic reagents stems from the low level expression of kinases, the labile activation state, which depends on protein phosphorylation and the poor specificity of antibodies against most phospho-epitopes, which indicate kinase activity. Consequently, most receptor tyrosine kinases (RTK) lack detection reagents for expression measurements in formalin-fixed paraffin embedded (FFPE) tissues, which is the most commonly obtained tissue preparation from patient cancers. It is becoming increasingly obvious that patient stratification for treatment with kinase inhibitors is a crucial for success with the anti-neoplastic activity of this group of agents. For a given solid tumor type, the frequency of cancers expressing the drug responsive target protein is small. Thus, if patients are not carefully selected for treatment, many agents could fail to demonstrate efficacy in phase II and phase III clinical trials.

The c-Met receptor is particularly difficult to measure in FFPE tissues because of poor reagent choices, insufficient validation of the performance of c-Met antibodies in FFPE tissues and sensitivity of c-Met to formalin-fixation. Given the promise of novel c-Met inhibitory agents in the clinic, companion diagnostics are needed to identify patients who would potentially benefit from these agents.

SUMMARY OF THE INVENTION

The present invention includes a monoclonal antibody "Met4", which is a monoclonal antibody produced by the hybridoma cell line deposited in the American Type Culture Collection under Accession Number PTA-7680. The present invention also includes an antigen binding fragment or derivative of said Met4 antibody. Further, the present invention includes a monoclonal antibody, or antigen-binding fragment or derivative thereof, that has all the identifying biological characteristics of the monoclonal antibody produced by the hybridoma cell line deposited in the American Type Culture Collection under Accession Number PTA-7680; a monoclonal antibody specific for Met, wherein the heavy chain and/or light chain variable region of said antibody, or an antigen binding site of said variable regions, has all the identifying biological or structural characteristics of the corresponding regions or sites of the monoclonal antibody produced by the hybridoma cell line deposited in the American Type Culture Collection under Accession Number PTA-7680; a monoclonal antibody specific for Met that binds to the same epitope as the epitope to which the monoclonal antibody produced by the hybridoma cell line deposited in the American Type Culture Collection under Accession Number PTA-7680 binds (or an antigen binding fragment or derivative of said antibody); a monoclonal antibody that binds to Met at the amino acids identified in SEQ ID NO.1 as 236-239, or an antigen binding fragment or derivative of said antibody; and, a monoclonal antibody that binds to Met at the amino acids identified in SEQ ID NO.1 as 482-485, or an antigen binding fragment or derivative of said antibody.

Another invention includes, a composition comprising any of monoclonal antibodies, fragments, or derivatives described in the preceding paragraph. The monoclonal antibody, fragment, or derivative of this composition may be linked to a detectable moiety.

Further, the invention includes a diagnostically useful composition with the composition of the preceding paragraph; and a diagnostically acceptable carrier or excipient. Also, with this composition, the monoclonal antibody, fragment, or derivative may be linked to a detectable moiety.

A further invention includes a kit, having: (a) a first container with the monoclonal antibody produced by the hybridoma cell line deposited in the American Type Culture Collection under Accession Number PTA-7680, or fragment or derivative thereof; (b) a second container with a diagnostically or pharmaceutically-acceptable carrier or excipient; and (c) instructions for using the antibody to detect Met, diagnose, prognose, or evaluate a Met inhibitory agent. With this kit, the monoclonal antibody, fragment, or derivative may be linked to a detectable moiety. Also, this kit may include a second monoclonal antibody, fragment or derivative; which second monoclonal antibody, fragment or derivative binds to the monoclonal antibody, fragment, or derivative from the first container, and the second antibody may be labeled with a detectable moiety. Further, this also may include a Met-inhibitory agent.

The present invention also includes several methods. First is a method for detecting the presence of Met in a tissue or a biological sample, which tissue or sample is suspected of expressing Met, comprising the steps of: (a) providing a tissue or sample suspected of expressing Met; (b) providing the present inventive composition described herein; (c) contacting the tissue or sample with this composition and (d) detecting the presence of Met in the tissue or sample. Second is a method of diagnosing or prognosing a Met-related cancer in a patient having or suspected of having a Met-related cancer, comprising the steps of: (a) obtaining a tissue or a biological sample from said patient; (b) providing the present inventive composition described herein; (c) contacting the tissue or biological sample with this composition; (d) determining the expression level of Met in the tissue or sample; and (e) comparing the expression level to a suitable control. Finally is a method for determining the effectiveness of a Met-inhibitory agent, comprising the steps: (a) obtaining a first tissue sample from a patient having a Met-related cancer; (b) treating the patient with a Met inhibitory agent; (c) obtaining a post-treatment tissue sample from the patient; (d) providing the present inventive composition described herein; (e) contacting each of the first tissue or biological sample and the post-treatment tissue or sample with this composition; (f) determining the expression level of Met in each of the first tissue or biological sample and the post-treatment tissue or sample; and (g) comparing the Met expression level of the first tissue or biological sample with the Met expression level of the post-treatment tissue or sample to determine the effectiveness of said Met-inhibitory agent. In each of these methods, the tissue or biological sample or samples may be fixed in formalin.

Another invention includes the hybridoma cell line deposited in the American Type Culture Collection under Accession Number PTA-7680.

These and other features, advantages and objects of the present invention will be further understood and appreciated by those skilled in the art by reference to the following specification, claims and appended drawings.

BRIEF DESCRIPTION OF THE DRAWINGS

FIGS. 1A and 1B show sections of FFPE tissue blocks stained with Met4 (Panel A) or C28 (Panel B). Met expression specifically occurs in basal epithelial cells (long arrow shaft with closed arrow head), endothelial cells (closed arrow head, no shaft) and in the basolateral membrane of secretory cells (long arrow and opened arrow head). FIGS. 1C through 1F show immunofluorescent staining with Met4 and C28. Gastric cancer MKN45 cells (Met positive) and NIH3T3 cells (Met negative) were co-cultured and fixed with formalin. FIG. 1C shows Met4; FIG. 1D shows Brighfield; FIG. 1E shows Met C28; and FIG. 1F is an overlay of FIGS. 1C and 1E.

FIG. 3A is a Western blot of ovarian cancer cell lines probed with Met C-28. LC: loading control. RNA expression results commensurate to the observed protein expression are shown in FIG. 6. FIG. 3B shows immunohistochemical staining with C28 and Met4 of FFPE cell pellets from ovarian cancer cell lines. A brown color indicates positive Met receptor expression. Of note, all cell lines stain with Met C-28. In contrast Met4 reactivity correlates with Met expression measured in the Western blot. FIG. 1C is a graph showing a correlation between signal intensities of WB and IHC measurements. The WB was probed with the 3D4 monoclonal antibody (Zymed) and c-Met expression quantified using the LICOR system. IHC was performed with Met4 at 1:500 dilution (4 μg/ml). The Pearson correlation coefficient is 0.602.

FIG. 4A is a Western blot of ovarian cancer cell lines probed with Met C-28. β-tubulin is used as a loading control. FIG. 4B shows an immunohistochemical staining with Met4 of FFPE cell pellets. A brown color indicates positive Met receptor expression. U118: glioblastoma, SW1783: glioblastoma U373: glioblastoma, NIH3T3: mouse fibroblast, DBTRG: glioblastoma, U87: glioblastoma, S114: NIH 3T3 cells transfected with the human genes for HGF/SF and Met 23, MCF7: breast cancer.

DETAILED DESCRIPTION OF THE PREFERRED EMBODIMENTS

Figure 1:
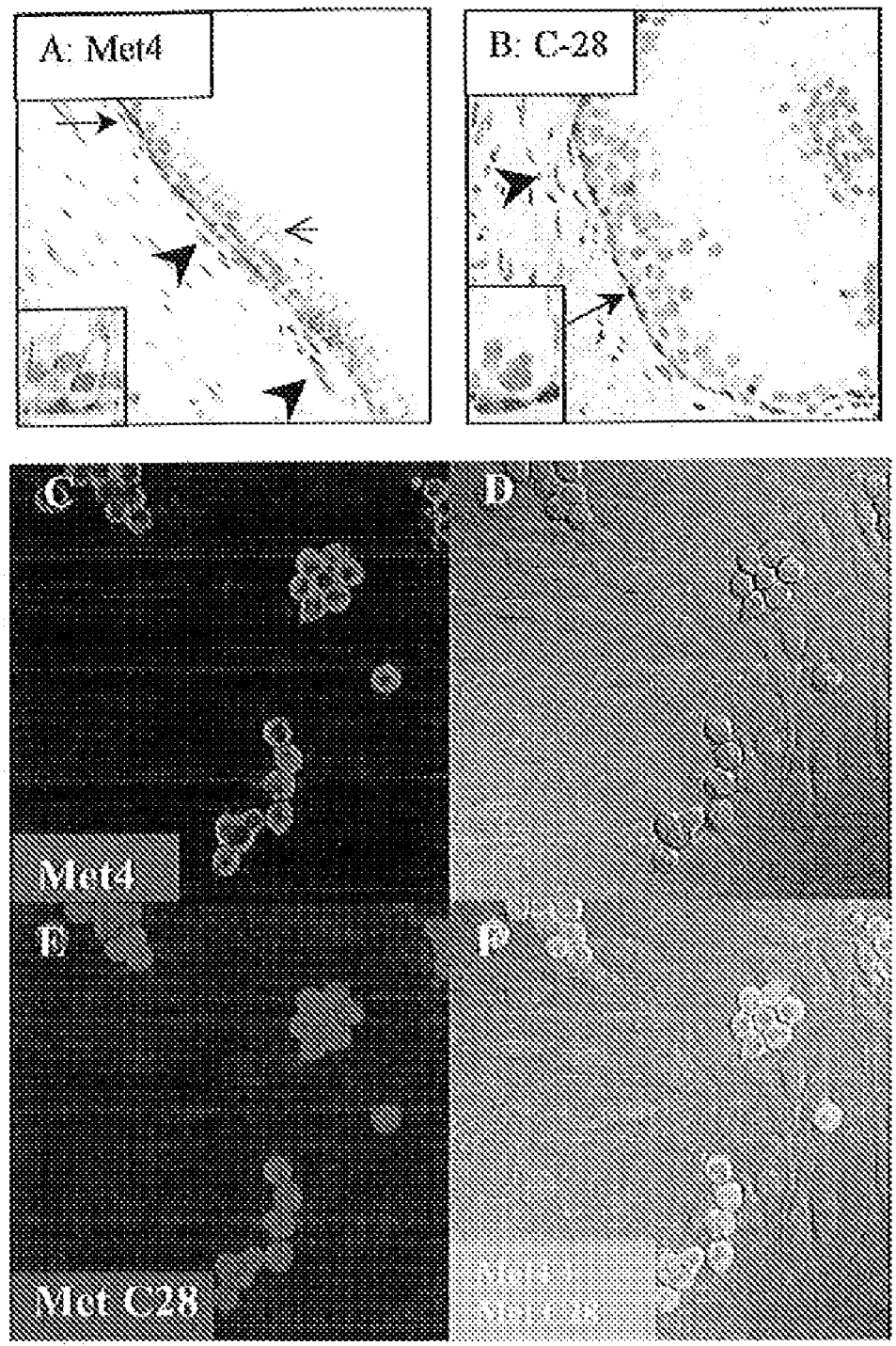
FIGS. 1A through 1F show the specificity of Met4.

The preferred embodiments of the present invention may be understood more readily by reference to the following detailed description of the specific embodiments and the Examples and Sequence Listing included hereafter.

The text file filed concurrently with this application, titled "VAN67P335.txt" contains material identified as SEQ ID NO: 1, which material is incorporated herein by reference. This text file was created on Aug. 24, 2007, and is 12,250 bytes.

All references, patents, patent publications, articles, and databases, referred to in this application are incorporated-by-reference in their entirety, as if each were specifically and individually incorporated herein by reference.

Unless defined otherwise, all technical and scientific terms used herein have the meaning commonly understood by one of ordinary skill in the art to which this invention belongs.

The "affinity" or "avidity" of an antibody for an antigen can be determined experimentally using any suitable method (See, for example, Berzofsky, et al, "Antibody-Antigen Interactions," In Fundamental Immunology, Paul, W E, Ed, Raven Press New York, N.Y. (1984), Kuby, Jams Immunology, W H Freeman and Company New York, N.Y. (1992), and methods described herein) The measured affinity of a particular antibody-antigen interaction can vary if measured under different conditions (e g, salt concentration, pH) Thus, measurements of affinity and other antigen-binding parameters (e g, K sub D, IC50) are preferably made with standardized solutions of antibody and antigen, and a standardized buffer.

As used herein, the term "biological sample" means organ or tissue extract and any fluid or other material derived from the body of a normal or diseased subject, such as, blood, serum, plasma, lymph, urine, saliva, tears, cerebrospinal fluid, milk, amniotic fluid, bile, ascites fluid, pus and the like.

The term "carrier" refers to a diluent, adjuvant, excipient, or vehicle with which the compound is administered. Such carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers.

The term "cell" is used in its usual biological sense, and does not refer to an entire multicellular organism. The cell can, for example, be in vitro, e.g., in cell culture. The cell can be prokaryotic (e.g., bacterial cell) or eukaryotic (e.g., mammalian or plant cell).

"Derivative" refers to either a protein or polypeptide (e.g., antibody) that comprises an amino acid sequence of a parent protein or polypeptide that has been altered by the introduction of amino acid residue substitutions, deletions or additions. The derivative protein or polypeptide possesses a similar or identical function as the parent polypeptide.

The phrase "detectable moiety" as used herein refers to a moiety that can be imaged and/or detected ex vivo or in vitro, by a procedure or modality described herein or known to one of skill in the art. As used herein, the detectable moiety can be directly or indirectly linked to the Met4 antibody of the present invention, to an anti-Met4 antibody, a binding fragment, or derivative thereof.

The term "diagnostically labeled" means that the antibody of the present invention, an anti-Met4 antibody, a binding fragment, or derivative thereof, has attached to it a diagnostically detectable label.

"Formaldehyde" means an organic chemical having the formula $CH_2O$. Formaldehyde is soluable in water. "Formalin" means an aqueous solution of formaldehyde.

"Fragment" refers to either a protein or polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 ammo residues, at least 70 amino acid residues, at least 80 amino acid residues, at least 90 amino acid residues, at least 100 amino acid residues, at least 125 amino acid residues, or at least 150 ammo acid residues) of the amino acid sequence of a parent protein or polypeptide. Examples of binding fragments encompassed within the term "antigen-binding fragment" of an antibody include (i) a Fab fragment, a monovalent fragment consisting of the VL, VH, CL and CH1 domains, (ii) a F(ab')2 fragment, a bivalent fragment comprising two Fab fragments linked by a disulfide bridge at the hinge region, (iii) a Fd fragment consisting of the VH and CH1 domains, (iv) a Fv fragment consisting of the VL and VH domains of a single arm of an antibody, (v) a dAb fragment (Ward et al (1989) Nature 341 544-46), which consists of a VH domain, and (vi) an isolated complementarity determining region (CDR) Camelid antibodies, and camelized antibodies can also be used. Such antibodies, e g, can include CDRs from just one of the variable domains described herein. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv), see, e g, Bird et al (1988) Science 242 423-26, Huston et al (1988) Proc Natl Acad Sci USA 85 5879-83). Such single chain antibodies are also intended to be encompassed within the term "antigen-binding fragment" of an antibody. These antibody fragments are obtained using conventional techniques known to those skilled in the art, and the fragments are evaluated for function in the same manner as are intact antibodies.

A protein or antibody that is "linked to a detectable moiety" is one that is bound, either covalently, through a linker, or through ionic, van der Waals or hydrogen bonds to a label such that the presence of the protein or antibody may be detected by detecting the presence of the label or detectable moiety bound to the protein or antibody.

A "monoclonal antibody or mAb" as used herein refers to an antibody that is part of a substantially, if not totally, homogeneous population of antibodies that are a product of a single B lymphocyte clone. mAbs are well known in the art and are made using conventional methods; see for example, Kohler and Milstein, Nature 256:495-497 (1975); U.S. Pat. No. 4,376,110; Harlow, E. et al., Antibodies: A Laboratory Manual, Cold Spring Harbor Laboratory Press, Cold Spring Harbor, N.Y., 1988); Monoclonal Antibodies and Hybridomas: A New Dimension in Biological Analyses, Plenum Press, New York, N.Y. (1980); H. Zola et al., in Monoclonal Hybridoma Antibodies: Techniques and Applications, CRC Press, 1982). mAbs maybe produced recombinantly as well, e.g., according to U.S. Pat. No. 4,816,567.

"Screening" or "Diagnosis" refers to diagnosis, prognosis, monitoring, characterizing, selecting patients (including participants in clinical trials), and identifying patients at risk for or having a particular disorder or clinical event or those most likely to respond to a particular therapeutic treatment, or for assessing or monitoring a patient's response to a particular therapeutic treatment.

A "small molecule" refers to a composition that has a molecular weight of less than 3 kilodaltons (kDa), and preferably less than 15 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention.

"Subject" or "patient" refers to a mammal, preferably a human, in need of treatment for a condition, disorder or disease.

The term "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. A "tumor" includes at least one tumor cell.

In the following description, reference will be made to various methodologies known to those of skill in the art of immunology, cell biology, and molecular biology. Publications and other materials setting forth such known methodologies to which reference is made are incorporated herein by reference in their entireties as though set forth in full. Standard reference works setting forth the general principles of immunology include A. K. Abbas et al., Cellular and Molecular Immunology (Fourth Ed.), W.B. Saunders Co., Philadelphia, 2000; C. A. Janeway et al., Immunobiology, The Immune System in Health and Disease, Fourth ed., Garland Publishing Co., New York, 1999; Roitt, I. et al., Immunology, (current ed.) C.V. Mosby Co., St. Louis, Mo. (1999); Klein, J., Immunology, Blackwell Scientific Publications, Inc., Cambridge, Mass., (1990).

Antibodies are polypeptides known also as immunoglobulin (Ig) molecules, which exhibit binding specificity to a specific antigen or epitope. The present use of the term "antibody" is broad, extending beyond the conventional intact 4-chain Ig molecule (characteristic of IgG, IgA and IgE antibodies). An antibody may occur in the form of polyclonal antibodies (e.g., fractionated or unfractionated immune serum) or a mAb (see below). Also included are Ig molecules with more than one antigen-specificity (e.g. a bispecific antibody formed by joining antigen-binding regions or chains from two different antibodies). Antibodies are typically polypeptides which exhibit binding specificity to a specific antigen. A native Ig molecule is typically a heterotetrameric glycoprotein, composed of two identical light (L) chains and two identical heavy (H) chains, with each L chain linked to a H chain by one interchain disulfide bond. Additional disulfide linkages bridge the two H chains. Each H and L chain has regularly spaced intrachain disulfide bonds. The N-terminus of each H chain and each L chain includes a variable (V) domain or region ($V_H$ and $V_L$). To the C-terminal side of the $V_H$ domains are a number of constant (C) domains ($C_H$); L chains have only a single C domain at its c-terminus (termed $C_L$). Particular amino acid residues form an interface between the VH and VL domains. Vertebrate L chains are assigned to one of two distinct types, also called isotypes, .kappa. and .lambda., based on the amino acid sequences of their C domains. Depending on the sequence of their CH domains, Igs are members of different classes: IgG, IgM, IgA, IgE and IgD, identified by their H chains referred to respectively as .gamma., .mu., .alpha., .epsilon. and .delta. Several subclasses or isotypes are also known, e.g., the IgG isotypes $IgG_1$, $IgG_2$, $IgG_3$, and $IgG_4$ (comprising the H chains known as .gamma.1, .iota.2, .gamma.3 and .gamma.4, respectively), or the IgA isotypes $IgA_1$, and $IgA_2$ (comprising the H chains al and .alpha.2, respectively).

When used to described domains or regions of antibody molecules, the term "variable" refers to amino acid sequences which differ among different antibodies and which are responsible for the antibody's antigen-specificity. Sequence the variability is evenly distributed throughout the V region but is typically greater in three particular regions, termed complementarity determining regions (CDRs) or hypervariable regions, that are present in VH and VL domains. The more highly conserved portions of V domains are called the framework (FR) regions. Each VH and VL domain typically comprises four FR regions. largely adopting a .beta.-sheet configuration, bonded to three CDRs, which form loops connecting, and in some cases forming part of, the .beta.-sheet structure. The CDRs in each chain are held in close proximity by the FR regions and, with the CDRs from the other chain, contribute to the formation of the antigen binding site (Kabat, E. A. et al., Sequences of Proteins of Immunological Interest, National Institutes of Health, Bethesda, Md. (1987)). The C domains are not involved directly in antigen binding but exhibit various effector functions, such as opsonization, complement fixation and antibody-dependent cellular toxicity.

Also included in the definition of an antibody is an antigen-binding fragment of an Ig molecule, including, Fab, Fab', F(ab').sub.2, Fv or scFv fragments, all well-known in the art. Fab and F(ab').sub.2 fragments lack the Fc fragment of intact antibody, clear more rapidly from the circulation, and may have less non-specific tissue binding than an intact antibody (Wahl et al., J. Nucl. Med. 24:316-325 (1983)). Fab fragments (and other forms of monovalent antibodies that have only a single antigen-binding site, have other known advantages, especially if it is preferred to avoid or limit internalization of the antibody into Met-bearing cells in vivo or activation of Met and the ensuing signal transduction pathways.

It will be appreciated that Fab, F(ab').sub.2, Fv and scFv fragments or forms of the antibodies useful in the present invention may be used for the detection, quantitation or isolation of Met proteins and the diagnosis or therapy of Met-expressing tumors in the same manner as an intact antibody. Conventional fragments are typically produced by proteolytic cleavage, using enzymes such as papain (for Fab fragments) or pepsin (for F(ab').sub.2 fragments). Fv fragments are described in (Hochman, J. et al., 1973, Biochemistry 12:1130-1135; Sharon, J, et al., 1976, Biochemistry 15:1591-1594). scFv polypeptides include the hypervariable regions from the Ig of interest and recreate the antigen binding site of the native Ig while being a fraction of the size of the intact Ig (Skerra, A. et al. (1988) Science, 240: 1038-1041; Pluckthun, A. et al. (1989) Methods Enzymol. 178: 497-515; Winter, G. et al. (1991) Nature, 349: 293-299); Bird et al., (1988) Science 242:423; Huston et al. (1988) Proc. Natl. Acad. Sci. USA 85:5879; U.S. Pat. Nos. 4,704,692, 4,853, 871, 4,94,6778, 5,260,203, 5,455,030. Also included as antibodies are diabodies and multispecific antibodies formed by combining more than one antigen-binding antibody fragment from antibodies of different specificity.

The present invention relates to an antibody named "Met4" which binds to an epitope in the extracellular domain of Met. Importantly, Met4 binds formalin-treated Met and can accurately quantify expression of denatured Met in formalin-fixed paraffin-embedded (FFPE) tissues. That is, Met4 is useful in diagnostic and prognostic tissue preparations. In one embodiment, the Met4 antibody is a companion diagnostic for Met-inhibitory drugs. Further, because of the reactivity of Met4 with the surface of Met-expressing cells, Met4 also is useful with in vivo molecular imaging applications.

The Met4 monoclonal antibody is produced by a hybridoma cell line that was deposited on Jun. 29, 2006, in the American Type Culture Collection (ATCC) under Accession Number PTA-7680. The address of the ATCC is 10801 University Blve., Manassas, Va., 20110-2209. The Met4 hybridoma was isolated based on a screening assay in FFPE prostate tissues and on the established specific expression of c-Met in certain subpopulations of prostate epithelial and endothelial cells (FIGS. 1A and B). This screening approach greatly increased the chances for obtaining an anti-Met antibody that is reactive with c-Met in FFPE tissues.

Figure 3:
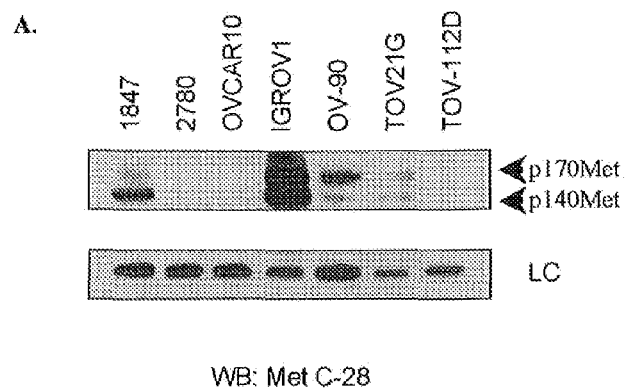
FIGS. 3A-3C compare Met4 and Met C-28 reactivity in formalin-fixed ovarian cancer cell lines.
Figure 3:
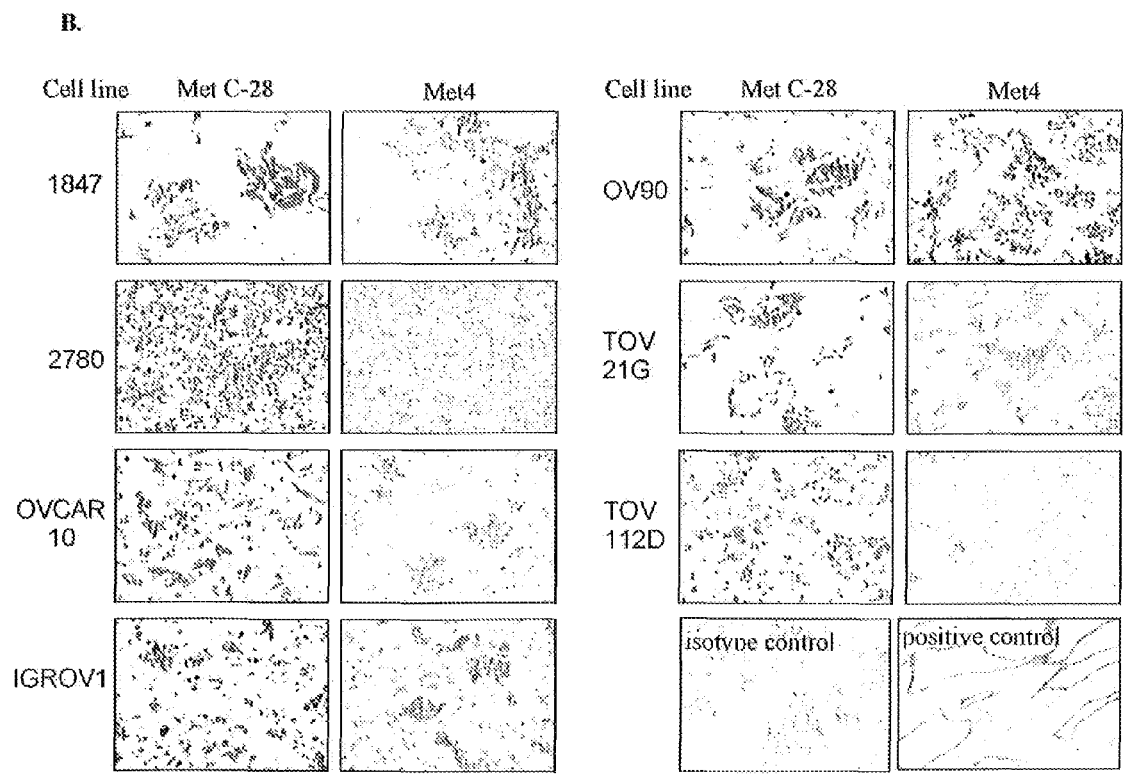
Figure 3:
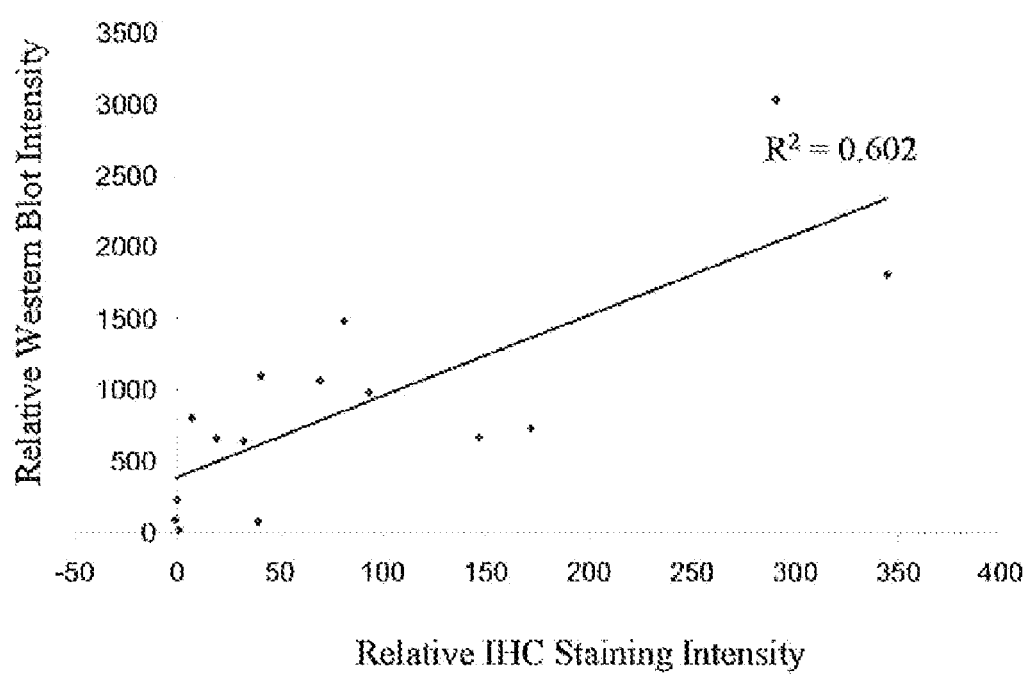

Thus, the Met4 antibody is useful for measurement of c-Met expression in FFPE tissues. Met4 demonstrates unique specificity for c-Met and quantifies c-Met expression levels in FFPE with good accuracy, as assessed by comparison of Met4 IHC and Western blotting signals ($\sigma$=0.602) (FIG. 3). Met4 staining was reproducible in replicate stains on the same day, on different days and when comparing two separate lots of Met4.

Most studies on c-Met expression in FFPE tissues employ various lots of the anti-Met C-28 polyclonal antibody from Santa Cruz. A systematic comparison of commercial c-Met antibodies, including three monoclonal antibodies and two separate lots of C-28 with the AQUA™ technology clearly demonstrated a greater than expected amount of variability in a breast cancer tissue microarray study[26]. One of the antibodies, DO-24 (Upstate), bound to the extracellular domain of c-Met, while the other recognized intracellular epitopes. Despite the fact that all antibodies bound to the Met receptor in a Western blot, their tissue reactivity was inconsistent between of breast cancer samples from the same patient. The most consistent results were obtained when comparing MAB3729 from Chemicon and a single lot of C28. MAB3729 possessed good reproducibility and a correlation coefficient of 0.94 for cores from the same cell line on adjacent TMA slides. When comparing two different lots of C28, a considerable lot-to-lot variability was noted, which compromises the clinical utility of C-28 and its utility to evaluate other c-Met antibodies by comparison. Therefore, there currently is no "gold standard' for testing of novel c-Met reactive antibodies in FFPE tissue preparations. However, Met4 has been validated in FFPE cell pellets by comparing quantification of c-Met by Western blotting to quantification by IHC staining (FIG. 3C).

Figure 2:
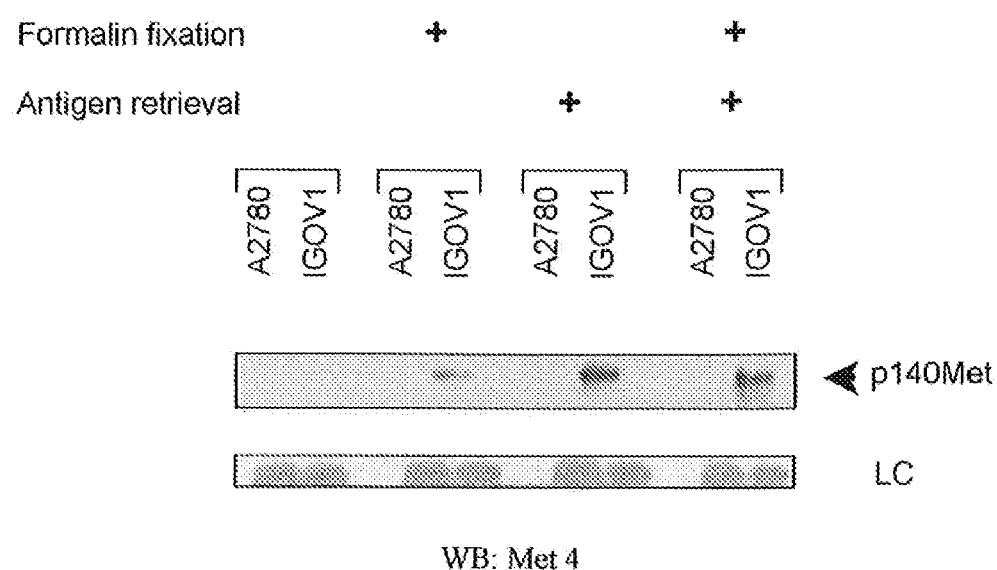
FIG. 2 is a Western Blot characterizing the Met4 epitope. Proteins in cell lysates of Met positive IGROV1 or Met negative A2780 ovarian cancer cells were Western blotted. The nitrocellulose membrane was treated with 10% formalin, boiled in antigen retrieval solution or subjected to both treatments sequentially. Treated membranes were probed with Met4 and developed using chemiluminescence. LC: loading control.

Met4 reacts with an epitope in the extracellular 25 to 567 amino acids of the Met receptor protein[41]. The Met4 binding site is sensitive to denaturation by boiling in SDS sample buffer, but is reestablished by either heat retrieval or formalin fixation (FIG. 2). The same heat retrieval is normally used with formalin-fixed tissues and vastly improves the antibody reactivity[50]. Boiling hydrolyzes bonds that are generated by formalin crosslinking and also causes refolding of proteins. Both formalin fixation and heat retrieval were effective in re-establishing the Met4 binding site within the denatured Met receptor protein after Western blotting. The reliability of an assay is particularly important when applying the measurement values to patient treatment decisions. Therefore, the intra- and interassay variability of the Met4 IHC assay was determined using cell pellets. Presumably the cellular material in a cell pellet is more homogenous than in a tissue section, since it consists of a single cell type. However, significant morphologic differences were observed between slides from cell pellets that were obtained from adjacent sections within the same tissue block. This variability increased the % CV of the intra- and interassay comparison.

Some Met antibodies that bind to the cytoplasmic domain of c-Met react with nuclear epitopes. A recent study demonstrates that the Met cytoplasmic domain can be cleaved and translocates to the nucleus[51]. However, the biologic function of the nuclear Met fragment, its kinase activity and targets and the broad clinical relevance of Met nuclear expression are uncertain. Nuclear expression of Met measured with the MAB3729 antibody in sections of breast cancer TMAs was associated with a decrease in 5-year survival from 75% to 65%[26]. Additional studies of nuclear c-Met expression are needed to evaluate its role as a biomarker.

While c-Met activation through somatic gene mutation or overexpression has been clearly observed in certain cancer types, they appear to be infrequent in primary ovarian cancers or gliomas. Overexpression of c-Met through duplication of the c-Met gene in double minute chromosomes was noted in 3/18 grade IV and 1/18 grade II gliomas[52]. In a different cohort, c-Met gene amplifications occurred in 3/11 gliomas[53]. As demonstrated in the Examples herein, increased c-Met expression was confirmed in high grade gliomas in the analysis of a glioma TMA. However unexpectedly, endothelial cells in the tumor vasculature of gliomas did not always demonstrate c-Met expression. In contrast to gliomas, all ovarian cancers expressed c-Met, and 7/28 demonstrated high c-Met expression. This observation differs from a previous study that observed less c-Met overexpression in endometroid ovary cancer and 10% high c-Met expression across the other histologic subtypes[54]. The mechanisms responsible for high c-Met expression and the activation state of c-Met in ovarian cancer are unknown. A comparison of c-Met RNA and protein expression in the cell lines panel for this study showed a poor correlation. It is unclear in ovarian cancer cell lines, whether high c-Met protein expression occurs because of amplification of the c-Met gene, increased transcription or post-translational retention of c-Met protein. The relevance of c-Met overexpression in ovarian cancer and its relationship to the therapeutic efficacy of Met inhibitory drug would best be evaluated in a clinical study that compares treatment responses and c-Met expression levels.

While c-Met activation through somatic gene mutation or overexpression has been clearly observed in certain cancer types, they appear to be infrequent in primary ovarian cancers or gliomas. Overexpression of c-Met through duplication of the c-Met gene in double minute chromosomes was noted in 3/18 grade IV and 1/18 grade II gliomas[52]. In a different cohort, c-Met gene amplifications occurred in 3/11 gliomas[53]. As demonstrated in the Examples herein, increased c-Met expression was confirmed in high grade gliomas in the analysis of a glioma TMA. However unexpectedly, endothelial cells in the tumor vasculature of gliomas did not always demonstrate c-Met expression. In contrast to gliomas, all ovarian cancers expressed c-Met, and 7/28 demonstrated high c-Met expression. This observation differs from a previous study that observed less c-Met overexpression in endometroid ovary cancer and 10% high c-Met expression across the other histologic subtypes[54]. The mechanisms responsible for high c-Met expression and the activation state of c-Met in ovarian cancer are unknown. A comparison of c-Met RNA and protein expression in the cell lines panel for this study showed a poor correlation. It is unclear in ovarian cancer cell lines, whether high c-Met protein expression occurs because of amplification of the c-Met gene, increased transcription or post-translational retention of c-Met protein. The relevance of c-Met overexpression in ovarian cancer and its relationship to the therapeutic efficacy of Met inhibitory drug would bets be evaluated in a clinical study that compares treatment responses and c-Met expression levels.

The present invention also relates to a method for detecting, in a biological sample, cells suspected to express Met, such as tumor cells. Various immunoassay techniques known in the art may be used, such as competitive binding assays, direct or indirect sandwich assays and immunoprecipitation assays conducted in either heterogeneous or homogeneous phases. See, for example, Zola, Monoclonal Antibodies: A Manual of Techniques, CRC Press, Inc. (1987) pp. 147-158). The antibodies used in this manner may be detectably labeled with a detectable label that produces, either directly or indirectly, a detectable signal. A skilled artisan can readily make suitable detection agents or labels for the Met4 antibody. The Met4 antibody can be detected in the tissue or sample by linking a detectable moiety to the Met4 antibody (or to an anti-Met4 antibody). The tissue or sample is contacted with the detectably labeled Met4 antibody (and with the anti-Met4 antibody, if the dectectable moiety instead is linked to the anti-Met4 antibody), and the presence of the detectable moiety in the tissue or sample is detected.

There are many different labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the antibodies used in the invention, or will be able to ascertain such, by routine experimentation. Diagnostically-labeled (e.g., radiolabeled) antibodies are effective.

Suitable detectable labels for diagnosis include radioactive, fluorescent, fluorogenic, chromogenic, or other chemical labels. Useful radiolabels, which are detected simply by gamma counter, scintillation counter, PET scanning or autoradiography include $^{3}H$, $^{124}I$, $^{125}I$, $^{131}I$, $^{35}S$ and $^{14}C$. In addition, $^{131}I$ is a useful therapeutic isotope (see below).

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, Handbook of Fluorescent Probes and Research Chemicals, Sixth Ed., Molecular Probes, Eugene, Oreg., 1996). Fluorescein, fluorescein derivatives and fluorescein-like molecules such as Oregon Green.™. and its derivatives, Rhodamine Green.™. and Rhodol Green.™., are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green.™. derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red.™. derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M. et al., Science 281:2013-2016 (1998), and quantum dots, e.g., zinc-sulfide-capped cadmium selenide (Chan, W. C. W. et al., Science 281:2016-2018 (1998)).

In another approach, the amino groups of an antibody are allowed to react with a reagent that yields a fluorescent product, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The antibodies can also be labeled for detection using fluorescence-emitting metals such as $^{152}Eu+$, or others of the lanthanide series. These metals can be attached to the peptide using such metal chelating groups as diethylenetri-aminepentaacetic acid (DTPA) or ethylenediamine-tetraacetic acid (EDTA). DTPA in anhydride form can readily modify the $NH_2$-containing antibodies.

Antibodies can also be made detectable by coupling them to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and acquorin.

In yet another embodiment, colorimetric detection is used, based on chromogenic compounds which have, or result in, chromophores with high extinction coefficients.

In situ detection of labeled antibody may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

One way to label an antibody is by linking it to an enzyme and using it in an enzyme immunoassay (EIA), or enzyme-linked immunosorbent assay (ELISA). Such assays are described in greater detail in: Butler, J. E., The Behavior of Antigens and Antibodies Immobilized on a Solid Phase (Chapter 11) In: STRUCTURE OF ANTIGENS, Vol. 1 (Van Regenmortel, M., CRC Press, Boca Raton 1992, pp. 209-259; Butler, J. E., ELISA (Chapter 29), In: van Oss, C. J. et al., (eds), IMMUNOCHEMISTRY, Marcel Dekker, Inc., New York, 1994, pp. 759-803 Butler, J. E. (ed.), IMMUNOCHEMISTRY OF SOLID-PHASE IMMUNOASSAY, CRC Press, Boca Raton, 1991; Voller, A. et al., Bull. WHO 53:55-65 (1976); Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980 Ishikawa, E. et al. (eds.) Enzyme Immunoassay, Kagaku Shoin, Tokyo, 1981. This enzyme, in turn, when later exposed to its substrate, will react with the substrate in such a manner as to produce a chemical moiety which can be detected, for example, by spectrophotometric, fluorometric or by visual means. Enzymes which are commonly used for this purpose include horseradish peroxidase, alkaline phosphatase, glucose-6-phosphate dehydrogenase, malate dehydrogenase, staphylococcal nuclease, .DELTA.-V-steroid isomerase, yeast alcohol dehydrogenase, .alpha.-glycerophosphate dehydrogenase, triose phosphate isomerase, asparaginase, glucose oxidase, .beta.-galactosidase, ribonuclease, urease, catalase, glucoamylase and acetylcholinesterase.

Chemical, including, covalent modifications of anti-Met antibodies are within the scope of this invention. One type of modification is introduced into the molecule by reacting targeted amino acid residues with an organic derivatizing agent that is capable of reacting with selected side chains or the N- or C-terminal residues.

Derivatization with bifunctional agents is useful for crosslinking the antibody (or fragment or derivative) to a water-insoluble support matrix or surface for use in a purification method (described below). Commonly used crosslinking agents include, e.g., 1,1-bis(diazo-acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropio-nate), and bifunctional maleimides such as bis-N-maleimido-1,8-octane. Derivatizing agents such as methyl-3-[(p-azidophenyl)dithio]propioimidate create photoactivatable intermediates that can crosslink when irradiated with light. Reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are used in protein immobilization.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chain (see, for example, T. E. Creighton, Proteins: Structure and Molecular Properties, W.H. Freeman & Co., San Francisco, (1983)), acetylation of the N-terminal amine, and amidation of any C-terminal carboxyl group. The modified forms of the residues fall within the scope of the present invention.

Also included herein are antibodies in which the native glycosylation pattern of the polypeptide have been altered. This means deletion of one or more carbohydrate moieties and/or adding one or more glycosylation sites that are not present in the native polypeptide chains. Protein glycosylation is typically N-linked (attached to an Asp side chain) or O-linked (attached to a hydroxyamino acid, most commonly Ser or Thr; possibly 5-hydroxyPro or 5-hydroxyLys). The tripeptide Asp-Z-Ser and Asp-Z-Thr (where Z is any amino acid but Pro) are recognition sequences for enzymatic attachment of the carbohydrate moiety to the Asp side chain. The presence of either of these sequences creates a potential N-glycosylation site. O-linked glycosylation usually involves binding of N-acetylgalactosamine, galactose, or xylose. Addition of glycosylation sites to the polypeptide may be accomplished by altering the native amino acid sequence to include e one or more of the above-described tripeptide sequences (for N-linked glycosylation sites) or addition of, or substitution by, one or more Serine or Threonine (for O-linked glycosylation sites). The amino acid sequence may be altered through changes at the DNA level, e.g., by mutating the DNA encoding the Ig polypeptide chain at preselected bases to generate codons that encode the desired amino acids. See, for example U.S. Pat. No. 5,364,934.

Chemical or enzymatic coupling of glycosides to the polypeptide may also be used. Depending on the coupling mode used, the sugar(s) may be attached to (a) Arginine and His, (b) free carboxyl groups, (c) free sulfhydryl groups such as those of Cys, (d) free hydroxyl groups such as those of Serine, Thr, or hydroxyPro, (e) aromatic residues such as those of Phe, Tyr, or Trp, or (f) the amide group of Gln. These methods are described in WO87/05330 (11 Sep. 1987) and in Aplin et al., CRC Crit. Rev. Biochem., pp. 259-306 (1981).

Removal of existing carbohydrate moieties may be accomplished chemically or enzymatically or by mutational substitution of codons (as described above). Chemical deglycosylation is achieved, for example, by exposing the polypeptide to trifluoromethanesulfonic acid, or an equivalent compound cleaves most or all sugars except the linking sugar (N-acetylglucosamine or N-acetylgalactosamine), while leaving the polypeptide intact. See: Hakimuddin et al., Arch. Biochem. Biophys., 259:52 (1987); Edge et al., Anal. Biochem. 118: 131 (1981). Any of a number of endo- and exo-glycosidases are used for enzymatic cleavage of carbohydrate moieties from polypeptides (Thotakura et al., Meth. Enzymol. 138:350 (1987)).

Glycosylation at potential glycosylation sites may be prevented by the use of the tunicamycin (Duskin et al., J Biol Chem, 257:3105 (1982) which blocks formation of N-glycosidic linkages.

Another type of chemical modification of the present antibodies comprises bonding to any one of a number of different nonproteinaceous polymers, such as polyethylene glycol (PEG), polypropylene glycol, or polyoxyalkylenes, in the manner described in U.S. Pat. Nos. 4,640,835; 4,496,689; 4,301,144; 4,670,417; 4,791,192 and 4,179,337 and WO93/00109.

Antibodies of the present invention can be used in a composition, including, the antibodies and a carrier.

In another aspect, the present invention relates to a method of diagnosing or prognosing a Met-related cancer. The method utilizes the Met4 antibody with a tissue or biological sample from a patient having or suspected of having a Met-related cancer, and Met4 or an anti-Met4 antibody is linked to a detectable moiety. The presence of the detectable moiety is detected in the tissue or sample from the patient, and the Met expression level in the tissue or sample is determined and compared to a suitable control. In the Examples below, the Met4 antibody is shown to be useful for detection of Met in several types of tumors. Based on the data presented in the Examples below, a skilled artisan can readily set up suitable controls as reference points of comparison for the expression of Met. One suitable control is the median or average expression level of many patients that either do not have cancer or do not have a particular type of cancer. The larger the number of patients used to establish a median or average level of Met expression as a control, the more accurate the diagnostic determination. Preferably, at least 25, 50, or 100 patients are used to establish the control level of expression.

The present invention also includes a method for monitoring or evaluating the effectiveness of a Met-inhibitory cancer treatment by determining whether the Met in the cells of a patient has been inhibited or eradicated. The method utilizes the Met4 antibody with a tissue or biological sample of a patient who has received a Met-inhibitory agent, and Met4 or an anti-Met4 antibody is linked to a detectable moiety. The presence of the detectable moiety is detected in the tissue or sample, and the Met expression level in the tissue or sample is determined and compared to pretreatment or earlier treatment levels of Met in the patient to determine whether the Met in the cells of the patient has been inhibited or eradicated.

Having now generally described the invention, the same will be more readily understood through reference to the following examples, which are provided by way of illustration, and are not intended to be limiting of the present invention, unless specified.

EXAMPLES

The specificity of Met4 for c-Met, the accuracy of c-Met quantification, and the reliability of the Met4 staining assay were evaluated in formalin-fixed and paraffin embedded (FFPE) cell pellets. Met4 was used to measure c-Met expression in a cohort of clinical tissue samples of ovarian cancers and gliomas. Specifically, in 22 cell lines, the Met4 signal from immunohistochemical analysis of FFPE cell pellets correlated with Western blot measurements of c-Met expression ($\sigma=0.603$). In contrast to Met4, the C-28 antibody from Santa Cruz reacted with FFPE cell pellets of cell lines that did not express c-Met. The technical reproducibility of repeated Met4 staining assays amounted to a % CV=37% for intra-assay and a % CV=21% for inter-assay variability. Ovarian cancers of the serous, endometroid and clear cell histologic subtypes stained positive with Met4 and in 25% the Met4 signal was high. Met4 staining was positive in cancer cells of 63% of gliomas, however Met4 staining expression in the glioma tumor vasculature was negative in most cases. Based on these results (i.e., because the Met4 antibody accurately and reproducibly measured c-Met expression in FFPE tissues), the Met4 antibody is useful for quantification of c-Met expression in a tissue or biological sample in a clinical context.

Example 1

Materials and Methods for Examples 1-5

Monoclonal Antibody Generation and Validation:
Recombinant protein Met 25-567H was prepared by Dr. Eric Xu's lab in Van Andel Institute. Met 25-567H construct (SEQ ID NO. 1, amino acids at positions 25-567) and purified Met 928 protein were from Dr. Ermanno Gherardi's lab in Cambridge Antibody Technology[41]. Recombinant fusion protein Met-IgG was purchased from R&D systems (Minneapolis, Minn.).

Mouse monoclonal antibodies against Met were produced by injecting BALB/c mice i.p. with native and denatured (boiling in SDS sample buffer) Met 25-567H in complete Freund's adjuvant, followed by two additional injections with incomplete Freund's adjuvant. After 1 month, a final injection was given i.p. and i.v. without adjuvant. Polyclonal antisera from immunized mice were tested by indirect immunofluorescence with formalin-fixed MKN45 (Met positive) and NIH3T3 (Met negative) cells. Spleen cells were fused with P3X63AF8/653 myeloma cells using standard techniques 4 days after final injection. Hybridoma cells were screened for reactivity to Met by ELISA and immunofluorescent staining.

Ten 96-well plates were coated with 2 µg/ml of Met25-567H in coating buffer (0.2M Na2CO3/NaHCO3, pH 9.6; 50 µl per well) overnight at 4° C. The plates were then blocked with PBS containing 1% BSA (200 µl/well) overnight at 4° C. Fifty microliters of hybridoma supernatant were added to wells for 1.5 h at room temperature (RT). Plates were washed twice in washing buffer (PBS with 0.05% Tween-20), and alkaline phosphatase-coupled goat anti-mouse IgG (Sigma) was added (50 µl/well) at 1:2000 dilution for 1.5 h at RT. After washing four times in washing buffer, phosphatase substrate CP-nitrophenyl phosphate (Kirkegaard & Perry Laboratories) was added for 30 min, and absorbance was measured at 405 nm. A total of 34 hybridomas having strong reactivity with Met25-567H (OD value greater than 2.0) were selected and tested on Met 928 by ELISA and 14 of them were positive. The 14 clones that react with both Met25-567H and Met928 were tested against Met-IgG by ELISA. Seven clones were found positive against all three Met proteins and were tested by immunofluorescent staining.

MKN45 and NIH3T3 cells were mixed and plated onto ten of 96-well plates and were cultured at 37° C. overnight. The cells were washed and fixed with 10% formalin on the next day. Fifty microliters of hybridoma supernatant from the seven clones were added to wells containing fixed cells for 1.5 h at 37° C. Plates were washed twice in washing buffer (PBS with 0.05% Tween-20), and Rhodamine Red-conjugated goat anti-mouse IgG (Jackson ImmunoResearch Lab) was added (30 µl/well) at 1:100 dilution for 1.5 h at 37° C. After washing two times in washing buffer, cells were examined under fluorescence microscope. Five clones were found positive and were picked and expanded. Supernatants of these five clones plus three clones from previous fusion were validated by immunohistochemistry on formalin-fixed normal human prostate tissue sections. Clone 8G6 (designated Met 4) gave the strongest signal and was sub-cloned twice and validated by ELISA against three recombinant Met proteins. Monoclonal antibody was produced using a bioreactor and was purified using protein-G affinity column by FPLC.

Immunohistochemistry:
Cell pellets: NIH 3T3, S114 (NIH 3T3 cells transfected with the human genes for HGF/SF and Met)23, SK-LMS-1/HGF (a human leiomyosarcoma cell line autocrine for human Met and human HGF/SF)24, SW-1783, U118, U87, U373, DBTRG (human brain glioblastoma), MCF-7 (breast cancer), ES-2, CaOV3, OV-90, SKOV3, TOV-112D, and TOV-21G (ovarian adenocarcinoma) cells were obtained from ATCC and cultured according to their media specifications. 1847, 2780, OVCAR10, OVCAR5, OVCAR3, PEO-1 cell lines (ovarian adenocarcinomas) were obtained from the Pacific Ovarian Cancer Research Consortium (Seattle, Wash.). 2008 was obtained from Dr. George Coucos (University of Pennsylvania). Cell layers were fixed in 10% neutral buffered formalin, scraped and embedded in HistoGel (Richard-Allan Scientific). HistoGel pellets were processed using the same settings as for large patient tissues and embedded in paraffin.

Human tissues: Formalin-fixed and paraffin embedded sections of ovarian cancer were obtained from the Pacific Ovarian Cancer Research Consortium under an IRB approved protocol. Tissue microarrays from gliomas were purchased from Cybrdi (Frederick, Md.). Antigen retrieval was performed with Target Retrieval Solution, pH9 (DAKO, Denmark) for 20 minutes in a Black and Decker vegetable steamer. The slides were loaded on the Dako Autostainer. All of the following incubations were performed at room temperature on the Autostainer: Endogenous peroxidase activity was blocked for 8 minutes with 3% hydrogen peroxide; a protein blocking step using Dako Serum-Free Protein Block was then completed for 10 minutes. The monoclonal mouse anti-human Met4 antibody was diluted 1:150 in Tris buffer/1% BSA for staining of TMA slides and 1:500 for staining of cell pellets. The Santa Cruz anti-Met polyclonal antibody was diluted 1:300. For the isotype control, purified mouse IgG was diluted to match the Met4 concentration. Biotinylated anti-mouse or anti-rabbit IgG (Vector Labs) secondary antibodies were diluted at 1:200 and were applied for 30 minutes. Then, Peroxidase-conjugated Streptavidin (Jackson ImmunoResearch) was used at 1:2,000 for 30 minutes. Finally, Dako Liquid DAB+ Substrate Chromagen System was applied for 7 minutes. The slides were counterstained with Dako Automation Hematoxylin for 2 minutes, dehydrated and coverslipped.

The scoring of immunohistochemically stained sections was done as described[42]. Briefly, a cumulative score was derived by multiplying the percentage of positive cells by the staining intensity. Cumulative scores were divided into categories from 0 to 3 and grouped by histologic subtype (ovarian cancer) or tumor grade (glioma).

Western Blot Analysis:

Subconfluent cells were lyzed in RIPA supplemented with protease and phosphatase inhibitors (Roche) buffer as described[43]. Protein lysates from cell lines were measured using a Bradford assay. Samples were measured on the same day using BSA standards ranging from 0 to 12 μg/ml. Samples were diluted such that 1-2 ml of sample provided a measurements within the linear range of the standard curve. Samples (50 mg) were resolved on a 4-15% gradient SDS-PAGE and transferred onto Immobilon™-P PVDF (Millipore, Billerica, Ma.) or nitrocellulose transfer membranes (Bio-Rad, Hercules, Calif.). Membranes for the formalin-fixed Western blot were fixed in 2% neutral buffered formalin Z-fix (Anatech Ltd., Battle Creek, Mich.) for 20 minutes and washed in PBS. Antigen retrieval was achieved with Target Retrieval Solution, pH9 for 20 minutes in a Black and Decker vegetable steamer. The membrane was blocked with 5% milk blocking buffer at room temperature and incubated with rabbit anti-human Met polyclonal antibody C-28 in 5% BSA at 1:250 dilution for 1.5 h at room temperature or at 1:1000 dilution over night; Alternatively, Met4 was used at 1:1,000 overnight and Zymed mouse anti-cMet clone:3D4 at 1:500. Donkey anti-rabbit IgG-HRP (Amersham) was used at 1:5,000 or AlexaFluor 680 goat anti-mouse IgG (Molecular Probes) was used at 1:10,000. Protein bands were detected by a chemiluminescence reagent (Pierce) or Odyssey® Infrared Imaging System (LI-COR Biosciences, Lincoln, Neb.). Images scanned on the Odyssey® Infrared Imaging System were scanned using the 700 nm channel at an intensity of 5.0. The signal intensity of the Met specific bands was measured using the 1D gel analysis module in the ImageQuant TL software. Background was subtracted using the "rolling ball" tool.

Digital Image Analysis of IHC-Stained Cell Pellets:

Slides of cell pellets stained with Met4 were spectrally imaged using a CRI Nuance camera system (www.cri-inc.com). 6-10 images were collected from each slide. Emission was measured between 420 nm and 720 nm in 20 nm increments. The resulting image cubes were converted to optical density units, and were mathematically unmixed into their individual DAB and hematoxylin components using spectrums deduced from control specimens and saved in a spectral library. The DAB, stain was pseudo-colored red to increase contrast. The hematoxylin was pseudo colored blue and the images were converted to pseudo-fluorescent format for quantification.

The spectrally unmixed images were then quantified with software developed by our laboratory that identified the mean DAB optical density as well as the number of pixels above background (as determined using the auto-thresholding algorithm of Ridler and Calvard[44]). Cell count was identified by counting the nuclei (as identified by hematoxylin counter stain) using the connected component algorithm[45] on pixels whose hematoxylin optical density was above background. A count of total nuclei was determined after using an auto high pass threshold filter. The threshold for positive Met4 staining was set using an intensity threshold filter value of 171 intensity units. This threshold parameter was defined using the negative control cell lines (A2780, OVCAR10 and TOV-112D) and restricting the number of positive pixels to 0.1%. This is similar to the PPA statistics[46]. These counts were then used to determine the percent positive Met4 cells for each sample pellet.

Statistical Analysis:

The Pearson's correlation coefficient was calculated using Microsoft© Excel software.

Example 2

Development of an Anti-c-Met Monoclonal Antibody for Quantification of c-Met in Formalin-Fixed Tissues The limitations of C-28, a polyclonal antibody from Santa Cruz, which has been used to measure Met expression in most in vitro and immunohistochemical studies, motivated our development of a monoclonal antibody (mAb) for measurement of c-Met protein expression in patient cancers for clinical applications, including molecular imaging and immunohistochemistry in formalin-fixed tissues. The immunogen was designed to obtain c-Met antibodies that react with the extracellular domain of the Met receptor, since this provides the most direct measurement to evaluate the abundance of c-Met expression on the cell surface. The resulting mAbs overcome the lot-to-lot variability of C-28 and the nuclear reactivity observed with antibodies that bind the Met cytoplasmic domain.

As a final screen to identify monoclonal antibodies that specifically bind the Met receptor in formalin-fixed and paraffin embedded (FFPE) tissues, sections of archival prostate tissues were stained with hybridoma supernatants (Table 1).

TABLE 1

Selection process for isolation of the Met4 hybridoma:

| | Hybridomas | Positive selection criteria | Negative selection criteria | Positive hybridoma clones for next screen |
|---|---|---|---|---|
| Splenocyte fusion | Half a spleen | HAT medium survival | | 960 |
| ELISA against Met25-567H | 960 | ELISA positive against Met25-567H | | 34 |
| ELISA against Met928 | 34 | ELISA positive against both Met25-567H and Met928 | | 14 |
| ELISA against Met-IgG | 14 | ELISA positive against 3 proteins: Met25-567H, Met928 and Met-IgG | | 7 |
| IF staining on MKN45/NIH3T3 formalin-fixed cells | 7 | MKN45 cells | NIH3T3 cells | 5 |
| IHC on prostate section | 8 (three of them were from previous fusion) | Basal epithelial cells Endothelial cells Plasma cells | Secretory cells Extracellular matrix Intense stromal cells | 3/8 Met4 gave strongest specific staining |

Based on the distinct subcellular pattern of Met receptor expression in prostate[47, 48], monoclonal antibodies were selected that react with basal epithelial cells, atrophic luminal epithelial cells[49] and endothelial cells, and that delineate the basal-lateral plasma membrane of secretory epithelial cells (FIGS. 1A and B). Antibodies that bind to nuclear proteins, cytoplasmic proteins in secretory cells, or diffusely to proteins in the prostate stroma were excluded. The antibody that provided the most intense and specific signal was named Met4. Met4 reacts with the cytoplasm of basal epithelial cells and the plasma membrane of luminal epithelial cells (FIG. 1A, insert). Met4 was further validated by staining co-cultures of Met-reactive MKN45 cells and non-reactive NIH3T3 cells, that were fixed in 10% formalin. The immunofluorescent staining is specifically observed along the membrane of MKN45 cells and coincides with immunoreactivity of C-28 (Santa Cruz) (FIG. 1C-F).

Example 3

Specificity of Met4 for Reactivity with c-Met in Formalin-Fixed Cells

To confirm the reactivity of Met4 with the Met receptor protein, a Western blot was probed with Met4. By recapitulating conditions of formalin-fixation in tissues, Western blot membranes were treated with 10% formalin and underwent the same type of antigen retrieval as had been applied to tissue sections. Met4 did not react with denatured Met receptor protein in IGROV1 ovarian cancer cells, which express a large amount of c-Met. Formalin fixation or boiling of the membrane in antigen retrieval buffer increased Met4 binding to c-Met and revealed a 140 kDa c-Met band (FIG. 2). Met4 reacted nonspecifically with lower molecular weight bands, some of which also appeared in the Met receptor negative A2780 cell line. The immunofluorescence and Western blotting results demonstrate that Met4 binds to a specific epitope on Met that is sensitive to denaturation and that is re-established by formalin-fixation or antigen retrieval.

Figure 6:
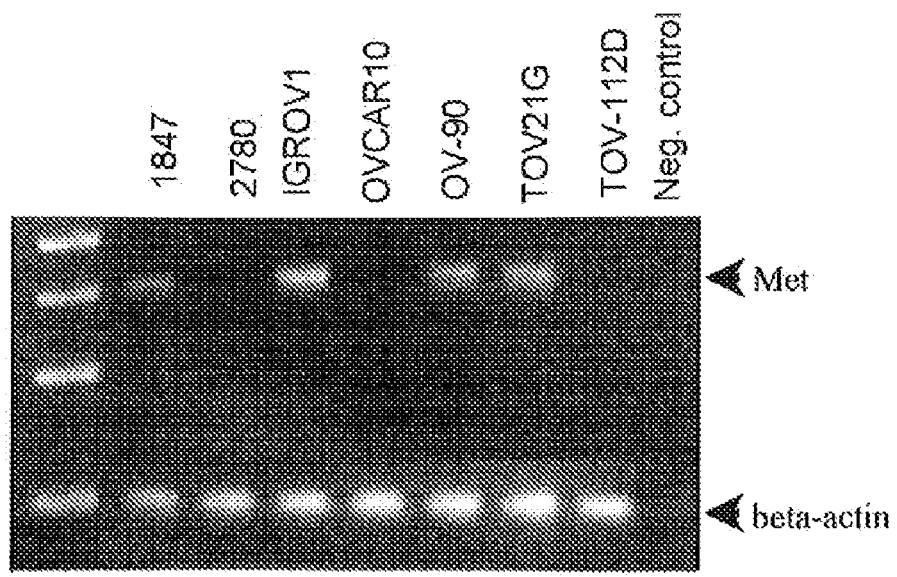
FIG. 6 is a Blot showing Met RNA expression in ovarian cancer cell lines. RNA was isolated from ovarian cancer cell lines. A fragment within the Met kinase domain was amplified from reverse transcribed RNA, amplified for 32 cycles and visualized on an agarose gel.

To further validate the specificity of Met4 in formalin-fixed cell preparations, panels of cell lines were analyzed. Cell lines were selected based on Met expression levels. The first panel consisted of 14 ovarian cancer cell lines. These cell lines express variable amounts of c-Met protein. A2780, OVCAR10 and TOV-112D do not express Met RNA or protein (FIG. 3A and FIG. 6) and IGROV1 and OVCAR5 cells highly express Met. To compare the specificities of Met4 and Met C-28 in formalin-fixed preparations to corresponding Western blot results, cell pellets of each cell line were processed in the exact same way as human tissues. Parallel sections of cell pellets on slides were stained with either Met4 or C-28 Met antibody. While C-28 Met reacted indiscriminately with all the cell lines, Met4 only stained those lines that were positive for Met expression on the Western blot and PCR analyses (FIG. 3B). To determine whether the reactivity of Met4 in formalin-fixed tissues is proportional to the level of expression of c-Met protein, digital measurements of the staining intensity from IHC-stained sections were compared with the amount of c-Met detected in a Western blot. After removal of outliers, which were attributed to clumps of Histogel in the cell pellet preparation, the Pearson correlation coefficient between IHC and WB was s=0.602 (FIG. 3C).

Figure 4:
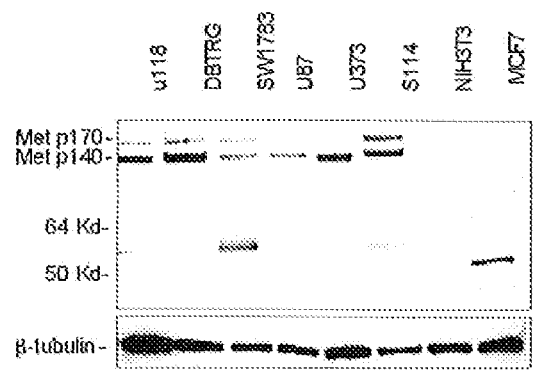
FIGS. 4A and 4B show the specificity of Met4 binding in formalin-fixed cell lines.
Figure 4:
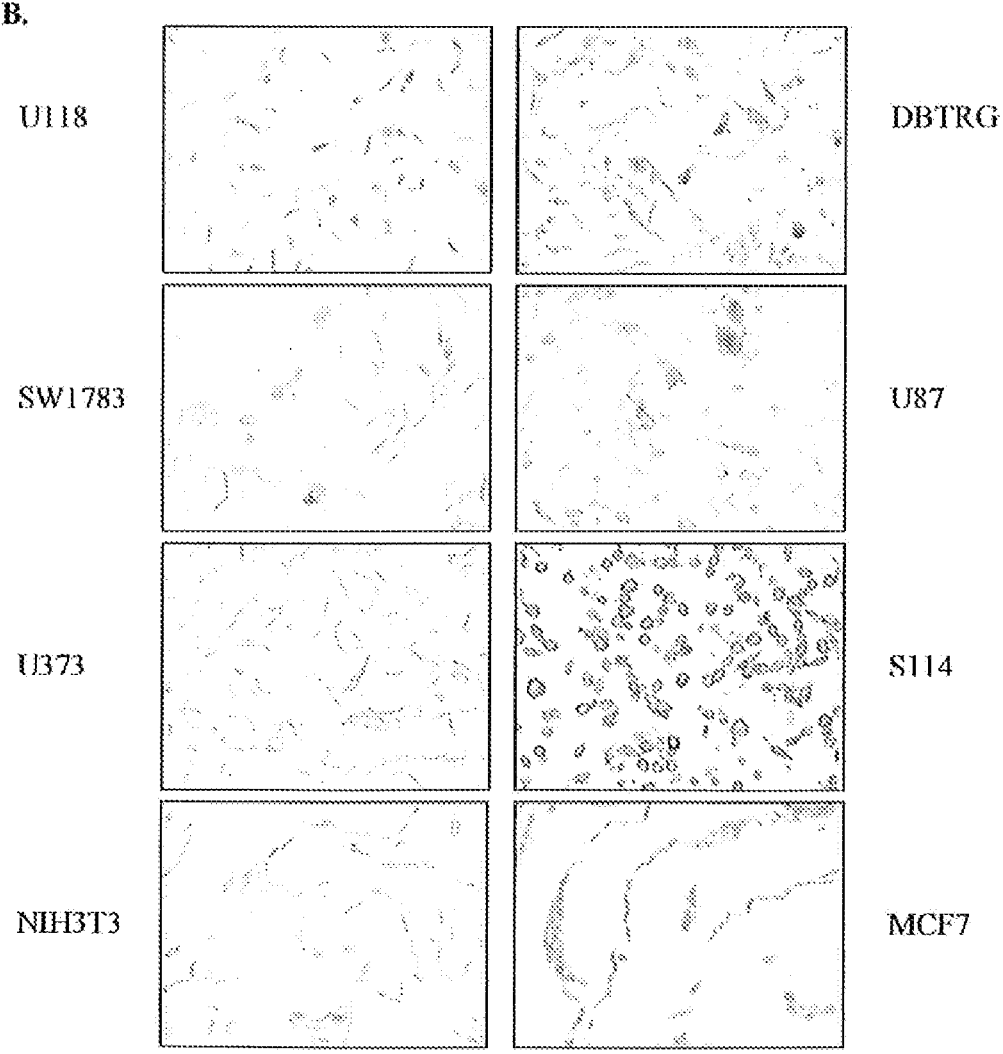

The specificity of Met4 was further tested in a variety of non-ovarian cell lines, most of which are glioblastoma cell lines (FIG. 4) and the results confirmed that Met4 reacts with c-Met expressing human, but not with c-Met positive mouse cells or with c-Met negative human cells.

Example 4

Reproducibility of Met4 Immunohistochemical Measurements

Since the results demonstrate that the novel Met4 antibody specifically binds c-Met in FFPE cell preparations, the reproducibility of staining in TOV21D cells, which express intermediate c-Met levels, was tested. The assay reproducibility is a critical factor in the development of an antibody for a clinical test. The consistency of Met4 staining intensities was analyzed in FFPE cell pellets amongst replicate stains on the same day (intra-assay variability) and slides stained on three different days (inter-assay variability). In addition, the staining results from two separate lots of Met4 antibody were compared. The two lots of purified antibody that were prepared separately from hybridoma culture medium revealed a correlation coefficient of s=0.75. The intra- and inter-assay variabilities consist of components of biological and technical (assay) variability, which cannot be separated in this analysis. Significant morphologic differences were observed amongst TOV21D cells in cell pellets on different days that affected the staining intensity of Met4. Consequently, the % CV's was 39% for the intra-assay variability. The variability of the Met4 assay performed on three separate days (interassay-variability) was % CV=21%. The inter-assay variability was calculated from average daily variabilities and less than the intra-assay variability.

Example 5

Met Expression in Ovarian Cancers and Gliomas

Figure 5:
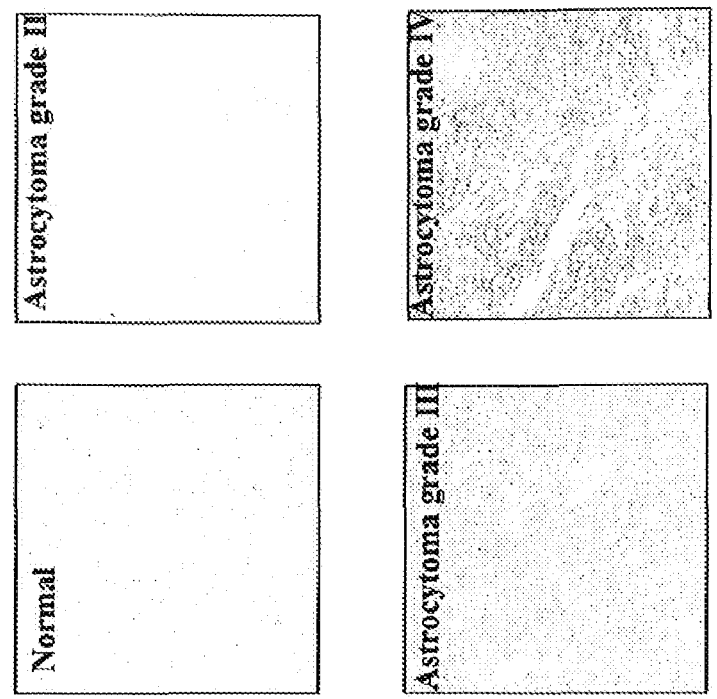
FIGS. 5A and 5B show Met4 reactivity in ovarian cancers and glioblastoma. Sections of ovarian cancers (FIG. 5A) or a glioma tissue microarray (FIG. 5B) were stained with Met4. Images were taken at 400× magnification. Negative and positive controls of prostate tissues were included in each staining and are shown in FIG. 3B (lower right panel). Summaries of tissue stains are shown in Tables 2 and 3.
Figure 5:
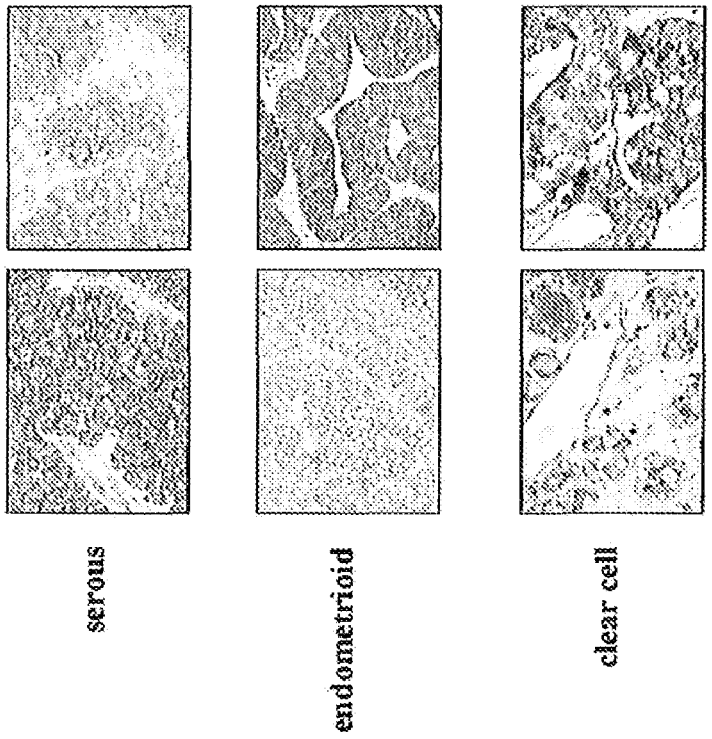

To evaluate the specificity of Met4 in archival FFPE tissues, sections of ovarian cancer tissues and a TMA of gliomas were analyzed. Met4 possessed high staining specificity for ovarian cancer cells, endothelial cells, a population of cells in the ovarian stroma and plasma cells. Nuclear staining was not observed (FIG. 5A). Histologic subtypes of ovarian cancers included serous, endometrioid and clear cell, but not mucinous cancers and all cancers were FIGO stage III-IV. All 29 ovarian cancers showed Met4 reactivity (Table 2).

TABLE 2

Met 4 Reactivity in Ovarian Cancers

| Score | Frequency (pts) | percentage | Histologic subtype | | |
|---|---|---|---|---|---|
| | | | Serous (% S) | Endometriod (% EM) | Clear cell (% CC) |
| 0 | | | | | |
| 1 | 9 | 30 | 3 (23%) | 4 (36%) | 2 (40%) |
| 2 | 12 | 45 | 6 (46%) | 5 (45%) | 1 (25%) |
| 3 | 7 | 25 | 4 (31%) | 2 (18%) | 1 (25%) |

Sections of ovarian cancer are stained with Met4. The overall score represents the average staining intensity of the section on a categorical scale of 0-3. (S—papillary serous carcinoma, EM—endometriod carcinoma, CC—clear cell carcinoma).

No significant statistical differences were observed in Met4 staining intensity across subtypes of ovarian cancer. Clear cell cancers, which are considered the most aggressive subtype, did not demonstrate greater reactivity than other histologic subtypes.

To evaluate the specificity of Met4 and expression of c-Met in brain tumors, a tissue array of gliomas was stained. The tissue microarray displayed 18 gliomas in triplicate cores. In addition, there were three cases of normal brain tissues (Table 3, FIG. 5B).

TABLE 3

Met 4 Reactivity of Gliomas (54 cores).

| Score | Frequency (Cores) | Percent (Cores) | Frequency (Patients) | Percent (patients) |
|---|---|---|---|---|
| 0 | 21 | 34 | 5 | 37 |
| 1 | 22 | 35 | 7 | 36 |
| 2 | 13 | 21 | 3 | 16 |
| 3 | 6 | 10 | 3 | 11 |
| Total | 62 | 100 | 18 | 100 |

A tissue microarray of 18 gliomas on triplicate cores was stained with the Met4 antibody. Met4 reactivity is assessed by multiplying the relative staining intensity and the percentage of positive cells. The overall score is expressed on a categorical scale from 0 to 3.

Neurons and reactive astrocytes stained strongly with Met4, while oligodendrocytes did not show Met staining. Surprisingly endothelial cells varied in Met positivity, including endothelial cells of the tumor vasculature. Five of 18 gliomas are Met negative and 3/18 stained strongly. All three were high-grade gliomas. Altogether, 70% of gliomas expressed c-Met and c-Met expression levels increased with tumor grade.

Example 6

Mapping of Met4 Epitope

Materials and Methods:
Met4 was prepared in PBS at a concentration of 2.0 mg/mL. Ph.D.-12 and Ph.D.-7 phage display peptide libraries were obtained from the New England Biolabs Phage Display Peptide Library kit. The −96 gIII sequencing primer, as well as host strain *E. coli* ER2738 were also obtained from this kit. All other solutions were prepared using SIGMA chemicals.

Figure 7:
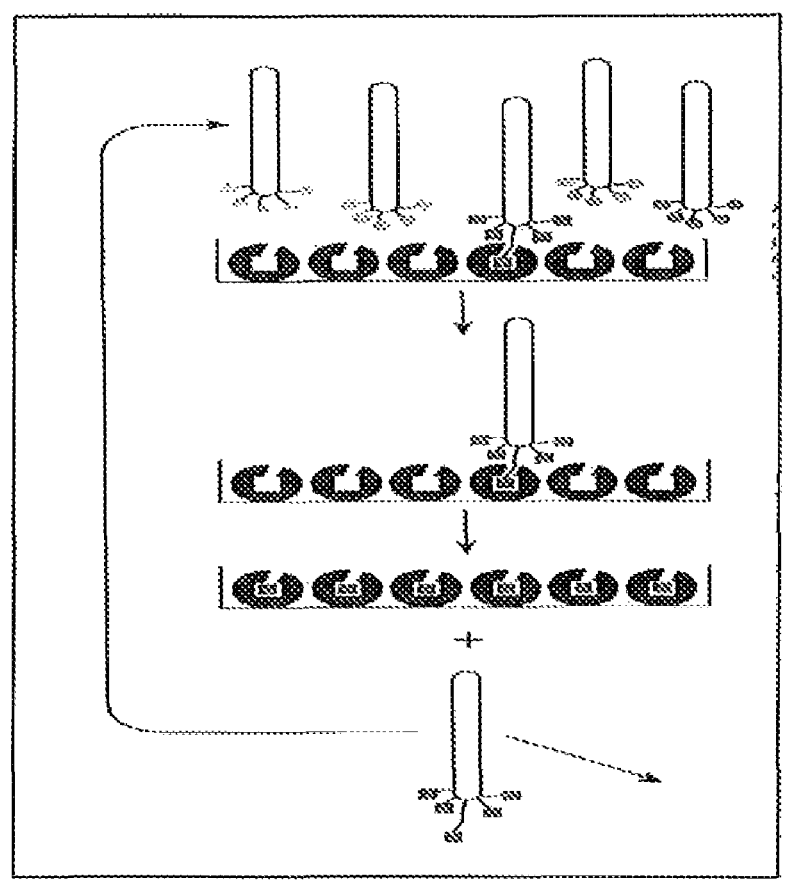
FIG. 7 shows panning with the phage display peptide library.
Figure 8:
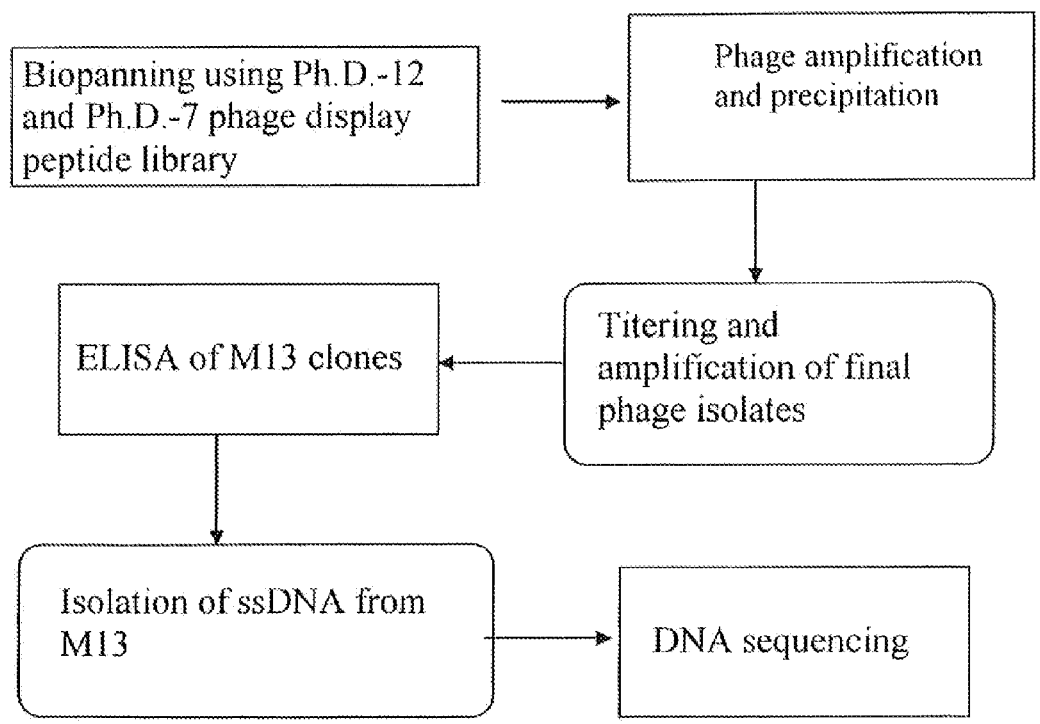
FIG. 8 is a flow diagram of the procedure for mapping the epitope of Met4.

FIG. 8 shows the methods used to map the Met4 epitope. First, a library of phage, each displaying a different peptide sequence, is exposed to a plate coated with the Met4 antibody. FIG. 7 shows biopanning with the phage display peptide library. Phage display allows for the existence of a link between random peptide sequences and the DNA that encodes these sequences. Biopanning is a selection technique in which phage-displayed peptides are exposed to a surface coated with a target molecule (enzyme, antibody, etc.).

Biopanning was performed using M13 Phage Display Library according to the New England Biolabs Phage display peptide Library Kit. Various steps included coating a 60×15 mm Petri dish with 100 µg/mL of Met4 antibody and exposing the plate to approximately 1×10 11 pfu of the M13 peptide library. Unbound phage was washed away with TBST, and specifically bound phage eluted with 10% Glycine HCl and BSA. As further described in more detail below, the eluted phage is amplified; the process is repeated for a total of 3-4 rounds; and, finally, individual clones positive for the Met4 antibody were isolated and sequenced.

For phage amplification and precipitation, a 1:100 dilution of ER2738 culture was used for infection and amplification. The phage was precipitated with 20% polyethylene glycol, 2.5M NaCl. Phage specific for the Met4 antibody were taken through several binding/amplification cycles. Table 4 shows the phage number in pfu for initial input from the Ph.D.-12 Library as well as the output following each round of panning against Met4.

TABLE 4

| Phage input | Phage eluted from 1st round panning | Phage eluted from 2nd round panning | Phage eluted from 3rd round panning |
|---|---|---|---|
| 1 × 10¹¹ pfu | 1.5 × 10⁴ pfu | 6.0 × 10⁴ pfu | 1.1 × 10⁸ pfu |
| % Recovery | 0.000015% | 0.00006% | 1.1% |
| Enrichment Fold | 1.00 | 4X | 73333X |

Titering and amplification of final phage isolates was performed to ensure each phage clone corresponded to a single DNA sequence.

Figure 9:
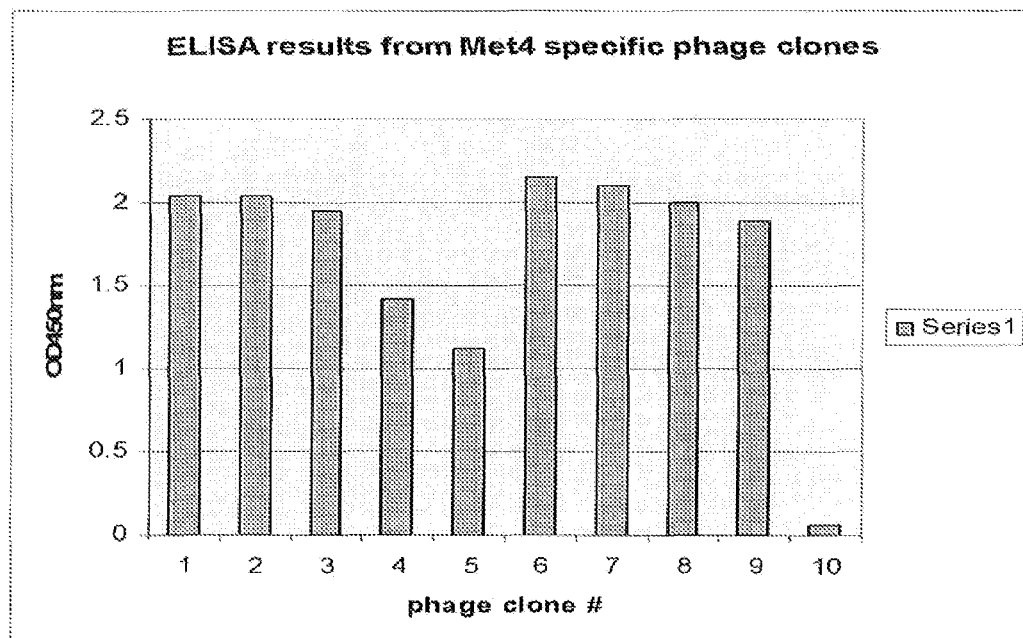
FIG. 9 is a bar graph showing OD450 nm values from ELISA of Met4 specific phage clones recovered from phage display-12 library as compared wild type M13.

ELISA of M13 colonies was performed according to the following methods: the Met4 antibody was exposed to individual M13 peptide display clones. A 1:5000 dilution of HRP conjugated anti M13 antibody in 1% Milk buffer was used as a secondary antibody. The peroxide substrate used was obtained from the Pierce TMB substrate kit. Plate was read at 450 nm using KC4 PC program. FIG. 9 is a bar graph showing OD450 nm values from ELISA of Met4 specific phage clones recovered from phage display-12 library as compared wild type M13.

ssDNA from M13 was isolated, as follows: the 8 M13 phage clones with the highest absorbance reading from ELISA were selected and their ssDNA molecules were isolated using the QIAprep Spin M13 protocol from the QIAprep M13 handbook by QIAGEN.

The epitopes were characterized through DNA sequencing of ultra-specific phage clones. DNA Sequencing was performed as follows: 2.0 µL isolated DNA from each M13 clone was combined with 1.0 µL of-the 28 gIII sequencing primer in PCR tubes. Samples were submitted to PCR and sequencing performed. The sequenced, Met4 specific M13 peptides (from the phage display-12 peptide library) were compared to the human Met extracellular HGF/SF binding domain sequence using the Sim program. Similarities between amino acid sequences are highlighted in Table 5.

TABLE 5

| | Human MET (aa 233-aa 243) N-SYIDVLPEFRD-C (SEQ. ID No. 2) | Seq. ID. Nos. | Human MET (aa 479-aa 488) N-FLLDSHPVSP-C | Seq. ID. Nos. |
|---|---|---|---|---|
| Met4 | | | | |
| phage clone 1 | TPPNSVDILPSR | 4 | | |
| phage clone 2 | AHGPFDHLPELH | 5 | | |
| phage clone 3 | SMWDFEPSSRPR | 6 | | |
| phage clone4 | | | MSQDWHPDLRVL | 7 |
| phage clone 5 | | | QPLRHHQDWAPD | 8 |
| phage clone 6 | | | DWDPSYRHRPPS | 9 |
| phage clone7 | | | SPCVDWGPHRAP | 10 |
| phage clone 8 | | | AWSDWSPSSRQT | 11 |
| phage clone 9 | | | TIRPDWSPALRA | 12 |

The Met4 Epitope(s):

This analysis revealed two possible Met4 epitopes. One epitope begins at amino acid 236 of Met (SEQ ID NO. 1) and spans four amino acids (236-239), while the other begins at amino acid 482 (SEQ ID NO. 1) and also spans four amino acids (482-485).

The above description is considered that of the preferred embodiment(s) only. Modifications of the invention will occur to those skilled in the art and to those who make or use the invention. Therefore, it is understood that the embodiment(s) shown in the drawings and described above is/are merely for illustrative purposes and not intended to limit the scope of the invention, which is defined by the claims as interpreted according to the principles of patent law, including the doctrine of equivalents.

REFERENCES

1. Birchmeier C, Birchmeier W, Gherardi E, Vande Woude G F: Met, metastasis, motility and more, Nat Rev Mol Cell Biol 2003, 4:915-925
2. Shu W, Guttentag S, Wang Z, Andl T, Ballard P, Lu M M, Piccolo S, Birchmeier W, Whitsett J A, Millar S E, Morrisey E E: Wnt/beta-catenin signaling acts upstream of N-myc, BMP4, and FGF signaling to regulate proximal-distal patterning in the lung, Dev Biol 2005, 283:226-239
3. Rosario M, Birchmeier W: How to make tubes: signaling by the Met receptor tyrosine kinase, Trends Cell Biol 2003, 13:328-335
4. Furge K A, Zhang Y W, Vande Woude G F: Met receptor tyrosine kinase: enhanced signaling through adapter proteins, Oncogene 2000, 19:5582-5589
5. Shinomiya N, Gao C F, Xie Q, Gustafson M, Waters D J, Zhang Y W, Vande Woude G F: RNA interference reveals that ligand-independent met activity is required for tumor cell signaling and survival, Cancer Res 2004, 64:7962-7970
6. Lutterbach B, Zeng Q, Davis L J, Hatch H, Hang G, Kohl N E, Gibbs J B, Pan B S: Lung cancer cell lines harboring MET gene amplification are dependent on Met for growth and survival, Cancer Res 2007, 67:2081-2088
7. Ma P C, Jagadeeswaran R, Jagadeesh S, Tretiakova M S, Nallasura V, Fox E A, Hansen M, Schaefer E, Naoki K, Lader A, Richards W, Sugarbaker D, Husain A N, Christensen J G, Salgia R: Functional expression and mutations of c-Met and its therapeutic inhibition with SU11274 and small interfering RNA in non-small cell lung cancer, Cancer Res 2005, 65:1479-1488
8. Peschard P, Fournier T M, Lamorte L, Naujokas M A, Band H, Langdon W Y, Park M: Mutation of the c-Cbl TKB domain binding site on the Met receptor tyrosine kinase converts it into a transforming protein, Mol Cell 2001, 8:995-1004
9. Ma P C, Maulik G, Christensen J, Salgia R: c-Met: structure, functions and potential for therapeutic inhibition, Cancer Metastasis Rev 2003, 22:309-325
10. Schmidt L, Duh F M, Chen F, Kishida T, Glenn G, Choyke P, Scherer S W, Zhuang Z, Lubensky I, Dean M, Allikmets R, Chidambaram A, Bergerheim U R, Feltis J T, Casadevall C, Zamarron A, Bemues M, Richard S, Lips C J, Walther M M, Tsui L C, Geil L, Orcutt M L, Stackhouse T, Lipan J, Slife L, Brauch H, Decker J, Niehans G, Hughson M D, Moch H, Storkel S, Lerman M I, Linehan W M, Zbar B: Germline and somatic mutations in the tyrosine kinase domain of the MET proto-oncogene in papillary renal carcinomas, Nat Genet 1997, 16:68-73
11. Jeffers M, Schmidt L, Nakaigawa N, Webb C P, Weirich G, Kishida T, Zbar B, Vande Woude G F: Activating mutations for the met tyrosine kinase receptor in human cancer, Proc Natl Acad Sci USA 1997, 94:11445-11450
12. Di Renzo M F, Olivero M, Giacomini A, Porte H, Chastre E, Mirossay L, Nordlinger B, Bretti S, Bottardi S, Giordano S, et al.: Overexpression and amplification of the met/HGF receptor gene during the progression of colorectal cancer, Clin Cancer Res 1995, 1:147-154
13. Kuniyasu H, Yasui W, Kitadai Y, Yokozaki H, Ito H, Tahara E: Frequent amplification of the c-met gene in 13. scirrhous type stomach cancer, Biochem Biophys Res Commun 1992, 189:227-232
14. Naldini L, Weidner K M, Vigna E, Gaudino G, Bardelli A, Ponzetto C, Narsimhan R P, Hartmann G, Zarnegar R, Michalopoulos G K, et al.: Scatter factor and hepatocyte growth factor are indistinguishable ligands for the MET receptor, Embo J 1991, 10:2867-2878
15. Rosen E M, Knesel J, Goldberg I D: Scatter factor and its relationship to hepatocyte growth factor and met, Cell Growth Differ 1991, 2:603-607
16. Zhuang Z, Park W S, Pack S, Schmidt L, Vortmeyer A O, Pak E, Pham T, Weil R J, Candidus S, Lubensky I A, Linehan W M, Zbar B, Weirich G: Trisomy 7-harbouring non-random duplication of the mutant MET allele in hereditary papillary renal carcinomas, Nat Genet 1998, 20:66-69
17. Kang J Y, Dolled-Filhart M, Ocal I T, Singh B, Lin C Y, Dickson R B, Rimm D L, Camp R L: Tissue microarray analysis of hepatocyte growth factor/Met pathway components reveals a role for Met, matriptase, and hepatocyte growth factor activator inhibitor 1 in the progression of node-negative breast cancer, Cancer Res 2003, 63:1101-1105
18. Tsarfaty I, Alvord W G, Resau J H, Altstock R T, Lidereau R, Bieche I, Bertrand F, Horev J, Klabansky R L, Keydar I, Vande Woude G F: Alteration of Met protooncogene product expression and prognosis in breast carcinomas, Anal Quant Cytol Histol 1999, 21:397-408
19. Huang T J, Wang J Y, Lin S R, Lian S T, Hsieh J S: Overexpression of the c-met protooncogene in human gastric carcinoma-correlation to clinical features, Acta Oncol 2001, 40:638-643
20. Lo Muzio L, Farina A, Rubini C, Coccia E, Capogreco M, Colella G, Leonardi R, Campisi G, Carinci F: Effect of c-Met expression on survival in head and neck squamous cell carcinoma, Tumour Biol 2006, 27:115-121
21. Baykal C, Ayhan A, Al A, Yuce K, Ayhan A: Overexpression of the c-Met/HGF receptor and its prognostic significance in uterine cervix carcinomas, Gynecol Oncol 2003, 88:123-129
22. Kaposi-Novak P, Lee J S, Gomez-Quiroz L, Coulouarn C, Factor V M, Thorgeirsson S S: Met-regulated expression signature defines a subset of human hepatocellular carcinomas with poor prognosis and aggressive phenotype, J Clin Invest 2006, 116:1582-1595
23. Tolgay Ocal I, Dolled-Filhart M, D'Aquila T G, Camp R L, Rimm D L: Tissue microarray-based studies of patients with lymph node negative breast carcinoma show that met expression is associated with worse outcome but is not correlated with epidermal growth factor family receptors, Cancer 2003, 97:1841-1848
24. Lengyel E, Prechtel D, Resau J H, Gauger K, Welk A, Lindemann K, Salanti G, Richter T, Knudsen B, Vande Woude G F, Harbeck N: C-Met overexpression in node-positive breast cancer identifies patients with poor clinical outcome independent of Her2/neu, Int J Cancer 2005, 113:678-682
25. Gotte M, Kersting C, Radke I, Kiesel L, Wulfing P: An expression signature of syndecan-1 (CD138), E-cadherin and c-met is associated with factors of angiogenesis and lymphangiogenesis in ductal breast carcinoma in situ, Breast Cancer Res 2007, 9:R8
26. Pozner-Moulis S, Cregger M, Camp R L, Rimm D L: Antibody validation by quantitative analysis of protein expression using expression of Met in breast cancer as a model, Lab Invest 2007, 87:251-260
27. Ide T, Kitajima Y, Miyoshi A, Ohtsuka T, Mitsuno M, Ohtaka K, Miyazaki K: The Hypoxic Environment in Tumor-Stromal Cells Accelerates Pancreatic Cancer Progression via the Activation of Paracrine Hepatocyte Growth Factor/c-Met Signaling, Ann Surg Oncol 2007,
28. Rong S, Segal S, Anver M, Resau J H, Vande Woude G F: Invasiveness and metastasis of NIH 3T3 cells induced by Met-hepatocyte growth factor/scatter factor autocrine stimulation, Proc Natl Acad Sci USA 1994, 91:4731-4735
29. Jeffers M, Fiscella M, Webb C P, Anver M, Koochekpour S, Vande Woude G F: The mutationally activated Met receptor mediates motility and metastasis, Proc Natl Acad Sci USA 1998, 95:14417-14422
30. Smolen G A, Sordella R, Muir B, Mohapatra G, Barmettler A, Archibald H, Kim W J, Okimoto R A, Bell D W, Sgroi D C, Christensen J G, Settleman J, Haber D A: Amplification of MET may identify a subset of cancers with extreme sensitivity to the selective tyrosine kinase inhibitor PHA-665752, Proc Natl Acad Sci USA 2006, 103:2316-2321
31. Welm A L, Kim S, Welm B E, Bishop J M: MET and MYC cooperate in mammary tumorigenesis, Proc Natl Acad Sci USA 2005, 102:4324-4329
32. Ma P C, Kijima T, Maulik G, Fox E A, Sattler M, Griffin J D, Johnson B E, Salgia R: c-MET mutational analysis in small cell lung cancer: novel juxtamembrane domain mutations regulating cytoskeletal functions, Cancer Res 2003, 63:6272-6281
33. Di Renzo M F, Olivero M, Martone T, Maffe A, Maggiora P, Stefani A D, Valente G, Giordano S. Cortesina G, Comoglio P M: Somatic mutations of the MET oncogene are selected during metastatic spread of human HNSC carcinomas, Oncogene 2000, 19:1547-1555
34. Lee J H, Han S U, Cho H, Jennings B, Gerrard B, Dean M, Schmidt L, Zbar B, Vande Woude G F: A novel germ line juxtamembrane Met mutation in human gastric cancer, Oncogene 2000, 19:4947-4953
35. Puri N, Ahmed S, Janamanchi V, Tretiakova M, Zumba O, Krausz T, Jagadeeswaran R, Salgia R: c-Met is a potentially new therapeutic target for treatment of human melanoma, Clin Cancer Res 2007, 13:2246-2253
36. Zhang Y W, Su Y, Volpert O V, Vande Woude G F: Hepatocyte growth factor/scatter factor mediates angiogenesis through positive VEGF and negative thrombospondin 1 regulation, Proc Natl Acad Sci USA 2003, 100:12718-12723
37. Grant D S, Kleinman H K, Goldberg I D, Bhargava M M, Nickoloff B J, Kinsella J L, Polverini P, Rosen E M: Scatter factor induces blood vessel formation in vivo, Proc Natl Acad Sci USA 1993, 90:1937-1941
38. Zou H Y, Li Q, Lee J H, Arango M E, McDonnell S R, Yamazaki S, Koudriakova T B, Alton G, Cui J J, Kung P P, Nambu M D, Los G, Bender S L, Mroczkowski B, Christensen J G: An orally available small-molecule inhibitor of c-Met, PF-2341066, exhibits cytoreductive antitumor efficacy through antiproliferative and antiangiogenic mechanisms, Cancer Res 2007, 67:4408-4417
39. Martens T, Schmidt N O, Eckerich C, Fillbrandt R, Merchant M, Schwall R, Westphal M, Lamszus K: A novel one-armed anti-c-Met antibody inhibits glioblastoma growth in vivo, Clin Cancer Res 2006, 12:6144-6152
40. Puri N, Khramtsov A, Ahmed S, Nallasura V, Hetzel J T, Jagadeeswaran R, Karczmar G, Salgia R: A selective small molecule inhibitor of c-Met, PHA665752, inhibits tumorigenicity and angiogenesis in mouse lung cancer xenografts, Cancer Res 2007, 67:3529-3534

41. Gherardi E, Youles M E, Miguel R N, Blundell T L, Iamele L, Gough J, Bandyopadhyay A, Hartmann G, Butler P J: Functional map and domain structure of MET, the product of the c-met protooncogene and receptor for hepatocyte growth factor/scatter factor, Proc Natl Acad Sci USA 2003, 100:12039-12044
42. Chen D, Adenekan B, Chen L, Vaughan E D, Gerald W, Feng Z, Knudsen B S: Syndecan-1 expression in locally invasive and metastatic prostate cancer, Urology 2004, 63:402-407
43. Gmyrek G A, Walburg M, Webb C P, Yu H-M, You X, Vaughan E D, Vande Woude G F, Knudsen B S: Normal and Malignant Prostate Epithelial Cells Differ in Their Response to Hepatocyte Growth Factor/Scatter Factor, Am J Pathol 2001, 159:579-590
44. Ridler T, Calvard S: Picture thresholding using an iterative selection method., IEEE Trans on Systems Man and Cybernetics 1978, SMC 8:630-632
45. Russ J C: The image processing handbook. Edited by Boca Raton, Fla., CRC Press, 2002, 732 p.p
46. Altstock R T, Stein G Y, Resau J H, Tsarfaty I: Algorithms for quantitation of protein expression variation in normal versus tumor tissue as a prognostic factor in cancer: Met oncogene expression, and breast cancer as a model, Cytometry 2000, 41:155-165
47. Knudsen B S, Gmyrek G A, Inra J, Scherr D S, Vaughan E D, Nanus D M, Kattan M W, Gerald W L, Vande Woude G F: High expression of the Met receptor in prostate cancer metastasis to bone, Urology 2002, 60:1113-1117
48. Humphrey P A, Zhu X, Zarnegar R, Swanson P E, Ratliff T L, Vollmer R T, Day M L: Hepatocyte growth factor and its receptor (c-MET) in prostatic carcinoma, Am J Pathol 1995, 147:386-396
49. van Leenders G, van Balken B, Aalders T, Hulsbergen-van de Kaa C, Ruiter D, Schalken J: Intermediate cells in normal and malignant prostate epithelium express c-MET: implications for prostate cancer invasion, Prostate 2002, 51:98-107
50. Shi S R, Cote R J, Taylor C R: Antigen retrieval techniques: current perspectives, J Histochem Cytochem 2001, 49:931-937
51. Pozner-Moulis S, Pappas D J, Rimm D L: Met, the hepatocyte growth factor receptor, localizes to the nucleus in cells at low density, Cancer Res 2006, 66:7976-7982
52. Fischer U, Muller H W, Sattler H P, Feiden K, Zang K D, Meese E: Amplification of the MET gene in glioma, Genes Chromosomes Cancer 1995, 12:63-65
53. Moon Y W, Weil R J, Pack S D, Park W S, Pak E, Pham T, Karkera J D, Kim H K, Vortmeyer A O, Fuller B G, Zhuang Z: Missense mutation of the MET gene detected in human glioma, Mod Pathol 2000, 13:973-977
54. Sawada K, Radjabi A R, Shinomiya N, Kistner E, Kenny H, Becker A R, Turkyilmaz M A, Salgia R, Yamada S D, Vande Woude G F, Tretiakova M S, Lengyel E: c-Met overexpression is a prognostic factor in ovarian cancer and an effective target for inhibition of peritoneal dissemination and invasion, Cancer Res 2007, 67:1670-1679

What is claimed is:

1. A hybridoma cell line deposited in the American Type Culture Collection under Accession Number PTA-7680.

2. A monoclonal antibody that binds to cMet hepatocyte growth factor receptor (Met-specific mAb) produced by the hybridoma cell line deposited in the American Type Culture Collection under Accession Number PTA-7680, or an antigen-binding fragment of said Met-specific mAb.

3. An isolated Met-specific monoclonal antibody (mAb) that binds to cMet hepatocyte growth factor receptor (Met) at amino acids 236-239 of SEQ ID NO:1, or an antigen-binding fragment of said Met-specific mAb.

4. A composition comprising
(a) the Met-specific mAb or fragment of claim 2 or 3 and
(b) a diagnostically acceptable carrier or excipient.

5. The Met-specific mAb or fragment of claim 2 or 3, wherein the Met-specific mAb or fragment is linked to a detectable moiety.

6. The composition of claim 4, wherein the Met-specific mAb or fragment is linked to a detectable moiety.

7. A kit, comprising:
   (a) a first container comprising the Met-specific mAb or fragment of claim 2 or 3;
   (b) a second container comprising a carrier for said Met-specific mAb or fragment; and
   (c) instructions for using the Met-specific mAb or fragment to detect or measure Met in a sample or to diagnose a Met-related disease.

8. The kit of claim 7 wherein the Met-specific mAb or fragment is linked to a detectable moiety.

9. The kit of claim 7 further comprising
   (d) a second antibody, or antigen-binding fragment thereof, which is specific for and binds to the Met-specific mAb or fragment.

10. The kit of claim 9 wherein the second antibody is labeled with a detectable moiety.

11. A method for detecting a presence of Met in a tissue sample or another biological sample from a subject, comprising
    (a) contacting the sample with the composition of claim 4, and
    (b) detecting the binding of the Met-specific mAb or fragment to said sample, wherein binding of the Met-specific mAb or fragment indicates the presence of Met in the sample.

12. The method of claim 11, wherein the Met-specific mAb or fragment is linked to a detectable moiety.

13. The method of claim 11, wherein the sample has been fixed by treatment with formaldehyde before the contacting step (a).

14. The method of claim 12 wherein the sample has been fixed by treatment with formaldehyde before the contacting step (a).

15. A method of diagnosing a cancer having increased Met expression in a subject, comprising:
    (a) contacting a tissue sample or other biological sample suspected of expressing Met from the subject with the composition of claim 4;
    (b) detecting or measuring the binding of the Met-specific mAb or fragment to the sample, thereby determining a presence or a level of Met in the sample; and
    (c) comparing the level of Met determined in (b) to a level of Met in a corresponding control sample from healthy subjects or subjects who do not have a disease with altered Met expression,
    wherein
    (i) the presence of Met determined in step (b) compared to an absence of Met in the control sample, or
    (ii) the increased level of Met determined in step (b) compared to the level of Met in the control sample
    is diagnostic of a cancer having increased Met expression.

16. The method of claim 15 wherein the sample has been fixed by treatment with formaldehyde before the contacting step (a).

\* \* \* \* \*